US008685671B2

(12) United States Patent
Kang et al.

(10) Patent No.: US 8,685,671 B2
(45) Date of Patent: Apr. 1, 2014

(54) **PROCESS FOR PRODUCING RECOMBINANT GLYCOPROTEINS BY CULTURING A *HANSENULA POLYMORPHA* MUTANT STRAIN**

(75) Inventors: Hyun Ah Kang, Daejeon (KR); Jeong Seok Park, Cheongju-si (KR); Moo Woong Kim, Daejeon (KR); Eun Jung Kim, Daejeon (KR); Hye Yun Moon, Daejeon (KR); Doo Byoung Oh, Daejeon (KR); Joo Hyung Heo, Daejeon (KR); Sang Ki Rhee, Seoul (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 0 days.

(21) Appl. No.: 13/451,223

(22) Filed: Apr. 19, 2012

(65) Prior Publication Data

US 2012/0202248 A1 Aug. 9, 2012

Related U.S. Application Data

(62) Division of application No. 12/091,217, filed as application No. PCT/KR2006/004395 on Oct. 26, 2006, now Pat. No. 8,187,858.

(30) Foreign Application Priority Data

Oct. 27, 2005 (KR) .................. 10-2005-0101992

(51) Int. Cl.
*C12P 21/00* (2006.01)
*C12N 15/81* (2006.01)
*C12N 15/90* (2006.01)
*C12N 1/19* (2006.01)
*C12N 9/10* (2006.01)

(52) U.S. Cl.
USPC ............... 435/71.1; 435/193; 435/254.11; 435/477

(58) Field of Classification Search
USPC ........... 435/455, 463, 325, 193, 69.1, 254.11; 530/350
See application file for complete search history.

(56) References Cited

U.S. PATENT DOCUMENTS

| 7,598,055 B2 | 10/2009 | Bobrowicz et al. |
| 2002/0137134 A1 | 9/2002 | Gerngross |
| 2005/0170452 A1 | 8/2005 | Wildt et al. |
| 2005/1017045 | 8/2005 | Wildt et al. |
| 2005/0208617 A1 | 9/2005 | Bobrowicz et al. |

FOREIGN PATENT DOCUMENTS

| KR | 1020040004089 A | 1/2004 |
| KR | 10-2005-0077689 A | 8/2005 |
| WO | 01/14522 A1 | 3/2001 |
| WO | 02/00879 A2 | 1/2002 |
| WO | 2004/003194 A2 | 1/2004 |
| WO | 2004/003205 A1 | 1/2004 |
| WO | 2005/073382 A1 | 8/2005 |

OTHER PUBLICATIONS

Souciet, et al., GenBank accession No. AL431946, 2001.
Nelissen, et al., "Classification of all putative permeases and other membrane plurispanners of the major facilitator superfamily encoded by the complete genome of *Saccharomyces cerevisiae*", FEMS Microbiology Reviews, 21:113-134, 1997.
Zhou, et al., "Global analysis of gene transcription regulation in prokaryotes", Cell Mol Life Sci, 63(19-20):2260-2290, 2006.
Kozak, M., "Initiation of translation in prokaryotes and eukaryotes", Gene 234:187-208,1999.
Kim, "Biosynthesis and maturation of yapsins in the methylotropic yeast hansenula polymo~ha", Master's Thesis, National Chungnam University, Korea, 2005.
Kim, et al., "Characterization of N-linked oligosaccharides assembled on secretory recombinant glucose oxidase and cell wall mannoproteins from the methylotrophic yeast *Hansenula polymorpha*' Glycobiology", 14(3):243-251, 2004.
Wildt, et al., "The humanization of N-glycosylation pathwaysin yeast", Nature Rev. Microbiol., 3:119-128, 2005.
Verostek, et al., "Structure of *Saccharomyces cerevisiae* alg3, sec18, Mutant Oligosaccharides", Journal of Biological Chemistry, 266(9):5547-5551, 1991.
Aebi, et al., "Cloning and characterization of the ALG3 gene of *Saccharomyces cerevisiae*", Glycobiology, 6(4):439-444, 1996.
Bekkers, et al., "The use of genetic engineering to obtain efficient production of porcine pancreatic phospholipase A 2 by *Saccharomyces cerevisiae*", Biochem. Biophy. Acta., 1089:345-351, 1991.
Chiba, et al., "Production of human compatible high mannose-type (Man5GlcNAc2) sugar chains in *Saccharomyces cerevisiae*", J. Biol. Chem., 273:26298-26304, 1998.
Kim, et al., "Functional characterization of the *Hansenula polymorpha* HOC1, OCH1, and OCR1 genes as members of the yeast OCH1 mannosyltransferase family involved in protein glycosylation", J. Biol. Chem., 281:6261-6272, 2006.
Davidson, et al., "Functional analysis of the ALG3 gene encoding the Dol-P-Man: Man5GlcNAc2-PP-Dol mannosyltransferase enzyme of *P. pastoris*", Glycobiology, vol. 14(5):399-401, 2004.

(Continued)

*Primary Examiner* — Delia Ramirez
(74) *Attorney, Agent, or Firm* — Lucas & Mercanti, LLP

(57) ABSTRACT

The present invention relates to a process for producing a human-type glycoprotein having reduced glycosylation by genetically manipulating an enzyme involved in glycosylation using a *Hansenula polymorpha* system. In detail, the present invention relates to a process for producing a human-type glycoprotein by identifying a dolichyl-phosphate-mannose dependent α-1,3-mannosyltransferase gene from *H. polymorpha*, constructing a *H. polymorpha* mutant strain producing a glycoprotein exhibiting reduced glycosylation by disrupting the identified gene, and subjecting the mutant strain to various genetic manipulations for the synthesis of human-type glycan.

5 Claims, 7 Drawing Sheets

(56) References Cited

OTHER PUBLICATIONS

Koury, "Sugar coating extends half-lives and improves effectiveness of cytokine hormones", Trends Botechnol., 21:462-464, 2003.

Levine, et at, "Isolation and characterization of a thermotolerant methanol-utilizing yeast", Applied Microbiology, 26(6): 982-990, 1973.

Oldenburg, et al., "Recombination-mediated PCR-directed plasmid construction in vivo in yeast", Nucleic Acid Res., 25:451-452, 1997.

Verostek, et al., "Glycoprotein biosynthesis in the alg3 *Saccharomyces cerevisiae* mutant", Journal of Biological Chemistry, 268(16):12104-12115, 1993.

Gemmill, et al., "Overview of N- and O-linked oligosaccharide structures found in various yeast species", Biochimica et Biophysicia Acta, 1426(2):227-237, 1999.

Oh, et al., "Glycoengineering of the methylotrophic yeast *Hansenula polymorpha* for the production of glycoproteins with trimannosyl core N-glycan by blocking core oligosaccharide assembly", Biotechnology Journal, 3(5):659-668, 2008.

August, et al., "The use of genetic engineering to obtain efficient production of porcine pancreatic phospholipase A2 by *Saccharomyces cerevisiae*", Biochimica et Biophysica Acta., 1089:345-351,1991.

Gellissen, et al., "Producion of recombinant proteins", Production of Recombinant Proteins, Novel Microbial and Eukaryotic Expression Systems, Gerd Gellissen (ed.), WILEY-VCH Verlag GmbH & Co. KGaA, 111-136, 2005.

Fig. 1

```
   1 atg gca gat gca aat gcg gat ata cag ccc gaa aca cgg ccg gag ctc aac tta gga aat
      M   A   D   A   N   A   D   I   Q   P   E   T   R   P   E   L   N   L   G   N
  61 gtc ctg ggc gat atc aag ttt gga ttg ttg tcg ctg ttc aac aac cct gag ttc tgc gcg
      V   L   G   D   I   K   F   G   L   L   S   L   F   N   N   P   E   F   C   A
 121 cca atc gcc gtc ttt ctg acc atc gca gag tcg ctt ctc ctc aag gcc gtg atc cat ttt
      P   I   A   V   F   L   T   I   A   E   S   L   L   L   K   A   V   I   H   F
 181 gtc ccc tac acc gag att gac tac agc acg tac atg cag cag atc gac caa att gag gct
      V   P   Y   T   E   I   D   Y   S   T   Y   M   Q   Q   I   D   Q   I   E   A
 241 gga gag ctt gac tac gcc aaa att agc ggc gac aca ggc cca att gtg tat ccc ggc gga
      G   E   L   D   Y   A   K   I   S   G   D   T   G   P   I   V   Y   P   G   G
 301 cat gtc tac ata tac tcg tgg atg aag tgg ttc acc aac ggg atg gac aac gtg cac gct
      H   V   Y   I   Y   S   W   M   K   W   F   T   N   G   M   D   N   V   H   A
 361 ggc cag cag att ttc agg tat cta tat ctg gcg aca ttt gtg cta act ctg gtt gcg tat
      G   Q   Q   I   F   R   Y   L   Y   L   A   T   F   V   L   T   L   V   A   Y
 421 ttc cag aca aat gtg cgg ttc aag ccg tac ctg ctc tac ttt ctg tgt ctg tcc aaa cgg
      F   Q   T   N   V   R   F   K   P   Y   L   L   Y   F   L   C   L   S   K   R
 481 ttg cac tcc atc tac gtg ctg cgg ctg ttc aac gac tgc ttt gcc acg ttt ctg atg gtg
      L   H   S   I   Y   V   L   R   L   F   N   D   C   F   A   T   F   L   M   V
 541 gct acg atc gtc gtt ctg cag cag gct gcc gtt ttg cgg cgc agg aag agc gct ctg ggc
      A   T   I   V   V   L   Q   Q   A   A   V   L   R   R   R   K   S   A   L   G
 601 gca gtg ctc acc ttt ttc agc gca cag ttg ttc agc tcc gcc gtc agc gtt aag atg aac
      A   V   L   T   F   F   S   A   Q   L   F   S   S   A   V   S   V   K   M   N
 661 gct ctg ctg tat ctg ccg ggc tac ttg gtg gtg gtg tac atg atc ctg gga gaa aac ctg
      A   L   L   Y   L   P   G   Y   L   V   V   V   Y   M   I   L   G   E   N   L
 721 ctg cac acg ctt gcc gtg att ggt ttc ggg tgt gca gtg cag gca ggc att aac tgg gac
      L   H   T   L   A   V   I   G   F   G   C   A   V   Q   A   G   I   N   W   D
 781 ttc ctg gcg gcc tcg gag acc aca aga gca cat ttc ctg cag aac gct ttc gac ttc agc
      F   L   A   A   S   E   T   T   R   A   H   F   L   Q   N   A   F   D   F   S
 841 cgt gct ttt ctg tac cgc tgg acg gtc aac tgg aag ttt gtg ccg gag ccc att ttc cgc
      R   A   F   L   Y   R   W   T   V   N   W   K   F   V   P   E   P   I   F   R
 901 agc cgc gag ttc cac acg ttg ctg ctg ctg gcg cac aca gcc gca ctg acg ttt ttc gcg
      S   R   E   F   H   T   L   L   L   L   A   H   T   A   A   L   T   F   F   A
 961 gtg tac aaa tgg agc agt aaa tct gtc acg gga aaa cca tcc acc aaa ttt atc aga gac
      V   Y   K   W   S   S   K   S   V   T   G   K   P   S   T   K   F   I   R   D
1021 gca ctg att ttc tac aaa gac acc ata ggc cca gaa aat gtg ata ctc tcc cca gaa agc
      A   L   I   F   Y   K   D   T   I   G   P   E   N   V   I   L   S   P   E   S
1081 ggc aga tac atc ttc tgg gtg atg gcg acg tcg aac ttg atc ggc gtc ttg ttc gcg cgc
      G   R   Y   I   F   W   V   M   A   T   S   N   L   I   G   V   L   F   A   R
1141 tcg ctg cac tac cag ttc ttg gcc tgg tat atg tac tcg ctg cca atg ctg ctg cag ctg
      S   L   H   Y   Q   F   L   A   W   Y   M   Y   S   L   P   M   L   L   Q   L
1201 ggc ggg ctg ccg tgg tac gca cag acg gcg ctc gtg gtg gtc cac gag tgg tgc tgg aac
      G   G   L   P   W   Y   A   Q   T   A   L   V   V   V   H   E   W   C   W   N
1261 gtg tac ccc agc aca gcg gcc agc tcg ttg ggc ctg gtg gca gtg ctt gcg aca gtg gtt
      V   Y   P   S   T   A   A   S   S   L   G   L   V   A   V   L   A   T   V   V
1321 ttg tcg cag ctc cgg tgt ggc ttc ggc aaa ccc aaa cag gaa
      L   S   Q   L   R   C   G   F   G   K   P   K   Q   E
```

PROCESS FOR PRODUCING RECOMBINANT GLYCOPROTEINS BY CULTURING A *HANSENULA POLYMORPHA* MUTANT STRAIN

CROSS-REFERENCE TO RELATED APPLICATIONS

This application is a divisional of U.S. Pat. No. 8,187,858, filed on Apr. 23, 2008, and issued on May 29, 2012, which is a 371 of PCT/KR2006/004395, filed Oct. 26, 2006, which claims the benefit of Korean Patent Application No. 10-2005-0101992, filed Oct. 27, 2005, the contents of each of which are incorporated herein by reference in their entirety.

TECHNICAL FIELD

The present invention relates to a process for producing a glycoprotein having a minimal core backbone of various human-type N-glycans, by genetically manipulating enzymes participating in glycosylation in *Hansenula polymorpha*.

BACKGROUND ART

Upon large-scale expression of therapeutic proteins, according to characteristics of host cells or target proteins, a target protein may vary in expression level, water solubility, expression sites, modification, and the like. Thus, the most suitable expression system for a target protein must be selected to establish an effective production system. Glycoproteins currently constitute about 70% of the recombinant therapeutic protein market, playing a leading role in the market. The components and structure of N-linked sugar moieties, which are attached to asparagine residues of glycoproteins, have been found to be major factors in determining the efficacy and stability of glycoproteins (Koury, M., Trends Biotechnol. 21, 462-464 (2003)). Animal cell culture technologies, which are capable of producing glycoproteins containing sugar moieties most similar to human's, are currently leading the market. However, there are several drawbacks to animal cell culture systems, which include low yield, high cost due to expensive culture media, risk of infection with viruses and prions, and a long period of time required to establish stable cell lines. Thus, animal cell culture systems have limited application in recombinant glycoprotein production.

As an alternative to animal cell culture systems, yeast expression systems have some advantages of being cost-effective, rapidly growing to high cell density in chemically defined medium, being easily genetically engineered, producing high yield of recombinant proteins, having no risk of infection with human or animal pathogens, and ensuring easy protein recovery. Moreover, as lower eukaryotes, yeasts share the early stages of the N-linked oligosaccharide of higher animal cells, and so could be utilized to produce several glycoproteins with therapeutic purpose. However, glycoproteins produced from yeast expression systems contain non-human N-glycans of the high mannose type, which are immunogenic in humans and thus of limited therapeutic value. In particular, this yeast-specific outer chain glycosylation of the high mannose type, denoted hyperglycosylation, generates heterogeneous recombinant protein products, which may make the protein purification complicated or difficult. Further, the specific activity of hyperglycosylated enzymes may be lowered due to the increased carbohydrate level (Bekkers et al., Biochem. Biophy. Acta.)089, 345-351 (1991)).

To solve the above problems, there is a need for glycoengineering, by which the yeast glycosylation pathway is remodeled to express glycoproteins having glycan structure similar to that of human glycoproteins. Glycoengineering was first applied to the traditional yeast, *Saccharomyces cercvisiae* which has the heavily hypermannosylated N-glycan structure composed of additional 50 to 200 mannose residues attached to the core oligosaccharide and decorated with the terminal α-1,3-linked mannoses highly immunogenic when injected to human body. Compared to *S. cerevisiae*, the methylotropic yeasts, *Hansenula polymorpha* and *Pichia pastoris*, are shown to produce N-linked glycans with shorter mannose outer chains and no α-1,3-linked terminal mannose (Kim et al., Glycobiol. 14, 243-251 (2004)). Therefore, the methylotrophic yeasts are considered superior expression hosts to the traditional yeast, *S. cerevisiae*, for the production of glycoproteins with therapeutic value. In addition, their excellent capacity in secreting recombinant proteins into the medium makes these methylotrophic yeasts favorable host systems for secretory protein production in the economical perspects.

*H. polymorpha* is a well known host for the production of recombinant hepatitis B vaccine, which has been approved for therapeutic use and already available on the market. At present, other *H. polymorpha*-derived therapeutic recombinant proteins, such as hirudin, elafin, and insulin, are launched in the market, demonstrating high potential of *H. polymorpha* as a practical host for the production of therapeutic recombinant proteins (Kang and Gellissen, Production of Recombinant proteins. Ed. G. Gellissen, pp. 111-136 (2005))However, technologies involving the remodeling of the yeast glycosylation pathway for the production of glycoproteins having human-type glycans have been mainly developed in *S. cerevisiae*, which is a well-characterized yeast, and *P. pastoris*, based on which a protein expression system is available (WO0114522, WO0200879, WO04003194, US2005/0170452, Wildt and Gemgross, Nature Rev. Microbiol. 3, 119-128 (2005)). In contrast, studies employing *H. polymorpha* in glycoengineering have seldom been conducted.

As an example of studies employing *H. polymorpha* in glycoengineering, the present inventors, prior to the present invention, cloned HpOCH1 and HpOCH2 genes, which play critical roles in the outer chain synthesis of *H. polymorpha*, and developed a process for producing a recombinant glycoprotein having a non-hyperglycosylated glycan structure using mutant strains having a disruption in any one of the genes (Korean Pat. Application No. 2002-37717 and No. 2004-6352, PCT Application PCT/KR2004/001819). However, a trimannose core structure containing three mannoses and two N-acetylglycosamine($Man_3GlcNAc_2$), which is the minimal common backbone of N-glycans, should be made in order to express glycoproteins having human compatible hybrid- and complex-type glycans.

In this regard, the present inventors identified a novel gene (HpALG3) coding for dolichyl-phosphate-mannose dependent α-1,3-mannosyltransferase, which is a key enzyme involved in the early stages of lipid-linked oligosaccharide biosynthesis prior to oligosaccharide addition to a glycoprotein, from the methylotrophic yeast *H. polymorpha*, and found that the manipulation of the gene alone or in combination of one or more genes, each coding for an enzyme involved in glycosylation, enables various manipulation of the glycosylation process of *H. polymorpha* and the preparation of glycoproteins having human-type glycans, thus leading to the present invention.

DISCLOSURE OF THE INVENTION

It is therefore an object of the present invention to provide a protein having the amino acid sequence represented by SEQ ID NO: 2, or 90% or higher homology therewith, and exhibiting dolichyl-phosphate-mannose dependent α-1,3-mannosyltransferase activity.

It is another object of the present invention to provide a nucleic acid coding for the protein, represented by SEQ ID NO: 1.

It is a further object of the present invention to provide a recombinant vector comprising the nucleic acid.

It is yet another object of the present invention to provide a *H. polymorpha* mutant strain which is deficient in a gene coding for dolichyl-phosphate-mannose dependent α-1,3-mannosyltransferase (HpALG3) and produces a glycoprotein having reduced glycosylation.

It is still another object of the present invention to provide a *H. polymorpha* mutant strain which is deficient in (a) a dolichyl-phosphate-mannose dependent α-1,3-mannosyltransferase gene and (b) one or more genes selected from among α-1,6-mannosyltransferase and α-1,2-mannosyltransferase genes.

It is still another object of the present invention to provide a *H. polymorpha* mutant strain which is deficient in (a) a dolichyl-phosphate-mannose dependent α-1,3-mannosyltransferase gene and (b) one or more genes selected from among α-1,6-mannosyltransferase and α-1,2-mannosyltransferase genes; and (c) overexpresses one or more glycan modifying enzymes.

It is still another object of the present invention to provide a process for preparing a glycoprotein with human-type glycans, comprising using the mutant strains.

It is still another object of the present invention to provide a glycoprotein with human-type glycans prepared according to the process.

BRIEF DESCRIPTION OF THE DRAWINGS

The above and other objects, features and other advantages of the present invention will be more clearly understood from the following detailed description taken in conjunction with the accompanying drawings, in which:

FIG. 1 shows a nucleotide sequence (SEQ ID NO: 1) and the deduced amino acid sequence (SEQ ID NO: 2) of the *H. polymorphs* ALG3 (HpALG3) gene, wherein four predicted transmembrane spanning regions are underlined;

FIG. 2 shows a multiple alignment of amino acid sequences of Alg3 protein analogues of *H. polymorpha* and other yeast strains (panel A), *S. pombe, Schizosaccharomyces pombe* Alg3 protein (SEQ ID NO: 13); *H. polymorpha, Hansenula polymorpha* Alg3 protein (SEQ ID NO: 14); *H. sapiens, Homo sapiens* Alg3 protein (SEQ ID NO: 15); *P. pastoris, Pichia pastoris* Alg3 protein (SEQ ID NO: 16); *S. cerevisiae, Saccharomyces cerevisiae* Alg3 protein (SEQ ED NO: 17). Amino acid sequence identities and similarities between *H. polymorpha* Alg3 protein and Alg3 proteins from other yeast strains and humans were also presented (panel B);

BEST MODE FOR CARRYING OUT THE INVENTION

Figure 3:
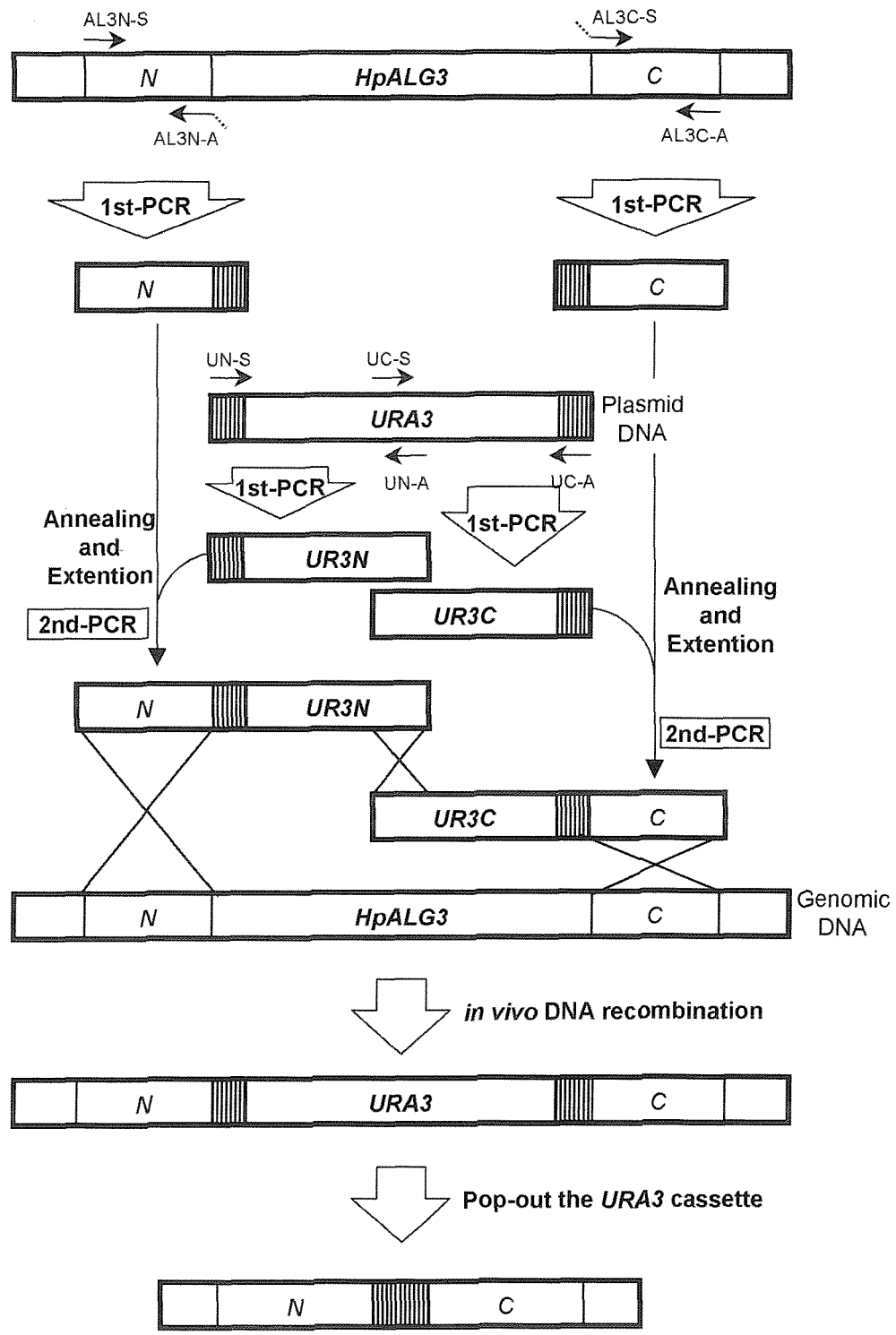
FIG. 3 is a diagram showing the disruption strategy of the *H. polymorpha* HpALG3 gene using fusion-PCR and in vivo DNA recombination.

The present invention relates to the technology of glycosylation pathway reconstruction of *H. polymorpha* to produce glycoprotein containing human-type glycan structure, which would be valuable for therapeutic purpose.

In order to develop a glyco-engineered strain, it is effective to reconstruct early glycosylation pathway of *H. polymorpha* by manipulating an enzyme acting on the early stages of oligosaccharide formation. In all eukaryotes, the early biosynthesis process of N-glycans, which occurs in the endoplasmic reticulum (ER), would be divided into two major phases. First, enzymes at the ER membrane sequentially add sugars to a lipid carrier called as dolichyl phosphate, to synthesize the initial oligosaccharide, $Glc_3Man_9GlcNAc_2$. The initial oligosaccharide is transferred to an appropriate asparagine residue of a nascent protein in the ER, and undergoes trimming steps to form the core oligosaccharide structure, $Man_8GlcNAc_2$, as attached to the glycoprotein, which is then transported to the Golgi apparatus.

The present inventors identified the HpALG3 gene coding for dolichyl-phosphate-mannose dependent α-1,3-mannosyltransferase, which is a key enzyme of the early lipid-linked oligosaccharide biosynthesis occurring in the ER membrane, in *H. polymorpha*. The present inventors are also the first to identify the function of gene product as dolichyl-phosphate-mannose dependent α-1,3-mannosyltransferase in *H. polymorpha*. The present inventors then constructed a mutant strain (Hpalg3 Δ) having a disruption in a gene coding for the enzyme, and found that the mutant strain of *H. polymorpha* effectively reduced the glycosylation of glycoproteins without any alteration in growth phenotypes. Further, a glycoengineered strain was developed to effectively produce a glycoprotein having the trimannose core oligosaccharide, which is the minimal core backbone of various human-type N-glycans. In addition, the present inventors found that, compared to a *P. pastoris* alg3 Δ mutant strain (R Davidson et al., Glycobiol. 14, 399-407, (2004)), the *H. polymorpha* alg3 Δ mutant strain provides a glycan structure consisting of fewer mannose residues and simpler and more uniform glycan profiling. This suggests that *H. polymorpha* is thus a more suitable host for the production of glycoproteins with human-type glycans.

The term "glycoprotein", as used herein, refers to a protein that is glycosylated on one or more asparagines residues or one or more serine or threonine residues, or is glycosylated on asparagine and serine or threonine residues. The term "reduced glycosylation", as used herein, means that when a glycoprotein is expressed in a methylotropic yeast strain, it has a carbohydrate moiety having a reduced size, particularly fewer mannose residues, in comparison with the case of being expressed in a wild-type methylotropic yeast.

In one aspect, the present invention relates to a protein having the amino acid sequence represented by SEQ ID NO: 2 or 90% or higher homology therewith and exhibiting dolichyl-phosphate-mannose dependent α-1,3-mannosyltransferase activity.

The present inventors found that dolichyl-phosphate-mannose dependent α-1,3-mannosyltransferase from *H. polymorpha* has the amino acid sequence represented by SEQ ID NO: 2. Dolichyl-phosphate-mannose dependent α-1,3-mannosyltransferase, having a wild-type sequence as well as proteins having 90% or higher homology with the wild-type sequence, as long as they have the enzyme activity, are included within the scope of the present invention.

In the present invention, the term "homoloy", as used for a dolichyl-phosphate-mannose dependent α-1,3-mannosyltransferase gene derived from *H. polymorpha*, is intended to indicate the degree of similarity to the amino acid sequence of a wild type, and includes an amino acid sequence having an identity of preferably 75% or higher, more preferably 85% or higher, even more preferably 90% or higher, and most preferably 95% or higher, with the amino acid sequence coding for dolichyl-phosphate-mannose dependent α-1,3-mannosyltransferase according to the present invention. This homology comparison may be performed manually or by using a commercially available comparison program. A commercially available computer program may express homology between two or more sequences in a percentage, and a homology (%) may be calculated for adjacent sequences.

In another aspect, the present invention relates to a nucleic acid coding for the protein.

The nucleic acid coding for dolichyl-phosphate-mannose dependent α-1,3-mannosyltransferase from *H. polymorpha* preferably has the nucleotide sequence represented by SEQ ID NO: 1. The present inventors registered the *H. polymorpha*-derived dolichyl-phosphate-mannose dependent α-1,3-mannosyltransferase (HpALG3) gene at GenBank under accession number DQ193533. Also, the present inventors constructed a recombinant vector containing the gene, pGEM-T Easy-HpALG3, and introduced the vector into *Escherichia coli* JM 109 by transformation. The resulting transformant was deposited at KCTC (Korean Collection for Type Cultures; Korea Research Institute of Bioscience and Biotechnology(KRIBB), 52, Oun-dong, Yusong-ku, Taejon, Korea) on Aug. 17, 2005, and assigned accession number KCTC 10835BP.

In a further aspect, the present invention relates to a recombinant vector which comprises a nucleic acid coding for a protein having the amino acid sequence represented by SEQ ID NO: 2 or 90% or higher homology therewith and exhibiting dolichyl-phosphate-mannose dependent α-1,3-mannosyltransferase activity.

The recombinant vector preferably comprises a nucleic acid coding for a protein having the amino acid sequence represented by SEQ ID NO: 2 or 90% or higher homology therewith and exhibiting dolichyl-phosphate-mannose dependent α-1,3-mannosyltransferase activity.

The term "vector", as used herein, refers to a means by which DNA is introduced into a host cell. The vector includes all ordinary vectors such as plasmid vectors, cosmid vectors, bacteriophage vectors, and viral vectors.

A suitable vector includes expression regulatory elements, such as a promoter, a start codon, a stop codon, a polyadenylation signal, and an enhancer, as well as signal sequences or leader sequences for membrane targeting or secretion, and may vary according to the intended use.

In yet another aspect, the present invention provides a host cell transformed with the recombinant vector, and preferably provides a transformed host cell deposited under accession number KCTC 10835BP.

In still another aspect, the present invention relates to a *H. polymorpha* mutant strain which is deficient in a gene coding for dolichyl-phosphate-mannose dependent α-1,3-mannosyltransferase and produces a glycoprotein exhibiting reduced glycosylation.

In detail, the present inventors obtained the gene (HpALG3) coding for dolichyl-phosphate-mannose dependent α-1,3-mannosyltransferase, which plays a critical role in the core oligosaccharide biosynthesis, using PCR, and then disrupted the HpALG3 gene using in vivo DNA recombination technique, thereby constructing a *H. polymorpha* mutant strain (Hpalg3Δ) producing a glycoprotein exhibiting reduced glycosylation.

The specific inactivation of a target gene on the genome may be achieved using a method established in the art, and the method is not particularly limited. The present inventors used homologous recombination in order to make a deletion specific for dolichyl-phosphate-mannose dependent α-1,3-mannosyltransferase gene. *H. polymorpha* was transformed with a vector containing a selection marker between N-terminal and C-terminal fragments of the gene encoding dolichyl-phosphate-mannose dependent α-1,3-mannosyltransferase to induce a homologous recombination between the genome and the vector. Selection markers useful in the present invention are not particularly limited, but include markers providing selectable phenotypes, such as drug resistance, auxotropy, resistance to cytotoxic agents, or surface protein expression. In the practice of the present invention, URA3 was used as a selection marker.

A *Hansenula polymorpha* alg3Δ mutant strain, which is deficient the dolichyl-phosphate-mannose dependent α-1,3-mannosyltransferase gene according to the method, expressed a glycoprotein having oligosaccharides (Man$_{5-8}$GlcNAc$_2$), which contains 5 to 8 mannose residues. The mannose residues in the oligosaccharide were remarkably reduced in comparison with 7 to 12 mannose residues of oligosaccharides derived from the *H. polymorpha* wild type. In addition, when the oligosaccharides obtained from the Hpalg3Δ mutant strain was treated with α-1,2-mannosidase and then α-1,6-mannosidase, they were converted to have a trimannose core oligosaccharide structure (Man$_3$GlcNAc$_2$), which is the minimal core backbone of human-type glycan structures. In comparison, *P. pastoris* alg3 Δ mutant strain expresses a glycoprotein having oligosaccharides (Hex$_{6-15}$GlcNAc$_2$), which contains 6 to 15 hexoses including mannose, some of the hexoses not being removed by mannosidase (Davidson et al., Glycobiol. 14, 399-407, (2004)). These indicate that *H. polymorpha* is more suitable as a strain in glycoengineering for the production of human hybrid-type and complex-type glycoproteins.

The term "human complex-type", as used herein, indicates all structures in which N-acetylglucosamine, galactose, and sialic acid are added successively to anyone of two terminal mannose residues of the trimannose core oligosaccharide, resulting in the formation of a bi- or more antennary structure. The term "human hybrid-type", as used herein, refers to a structure in which one or more antennas stretched from the trimannose core oligosaccharide are elongated or terminated only with mannose residues, and the remaining antennas have the ordered assembly of N-acetylglucosamine, galactose, and sialic acid.

The Hpalg3Δ mutant strain may be further manipulated to have various human-type glycan structures by glycosylation pathway remodeling.

As an attempt, an additional manipulation is possible in another gene involved in glycosylation in the background of Hpalg3Δ mutant strain. For example, a genetic deficit may be made in an α-1,6-mannosyltransferase gene, an α-1,2-mannosyltransferase gene, or both genes. In a detailed practice of the present invention, an Hpoch2Δalg3Δ double-deletion mutant strain, which is deficient in both HpOCH2 (encoding α-1,6-mannosyltransferase), and HpALG3, was constructed. The Hpoch2Δalg3Δ double-deletion mutant strain was found to have a glycoprotein having oligosaccharides ($Man_{4-6}GlcNAc_2$) with remarkably reduced mannose residues, that is, 4 to 6 mannose residues (panel B, FIG. 7).

In addition, the mutant strain may be transformed with an expression vector capable of expressing one or more proteins having enzyme activity involved in oligosaccharide modification in order to effectively synthesize human-type glycans. The trimannose core oligosaccharide ($Man_3GlcNAc_2$) may be generated by introducing heterologous genecs coding for enzymes which include, but are not limited to, α-1,2-mannosidase, mannosidase IA, mannosidase IB, mannosidase IC, and mannosidase II, and may also be made with a gene or a fragment thereof having cleavage activity for mannose residues. In a detailed practice of the present invention, when α-1,2-mannosidase was expressed in the Hpoch2Δalg3Δ double-deletion mutant strain, a recombinant glycoprotein having the trimannose core oligosaccharide was produced (panel C, FIG. 7). Various human hybrid-type and complex-type glycoproteins may be produced by adding N-acetylglucosamine, galactose, fucose, sialic acid, and the like to the trimannose core oligosaccharide, which is the common core backbone of human-type glycans.

Thus, N-acetylglucosamine may be added with N-acetyl glucosaminyltransferase I, N-acetyl glucosaminyltransferase II, and the like, galactose with galactosyltransferase, sialic acid with sialyltransferase, and fucose with fucosyltransferase. However, the present invention is not limited to these examples, and various genes capable of leading to oligosaccharide modification may be also used. Also, genes of biosynthetic pathways of substrates of the enzymes, such as UDP-acetylglucosamine, UDP-glactose and CMP-sialic acid, and genes encoding transporters transporting the substrates to the Golgi apparatus or ER are included. Their fragment sequences as well as the whole genes described above can be used as far as they encode functional regions showing their intrinsic activities.

In still another aspect, the present invention relates to processes for preparing a recombinant glycoprotein with human-type glycans, comprising using the *H. polymorpha* ALG3 deficient mutant strain.

Mutant strains suitable for use in the preparation of glycoproteins with human-type glycans include all types of the aforementioned mutant strains. A recombinant glycoprotein having human hybrid-type or complex-type glycans may be prepared using mutant strains which are constructed by expressing one or more genes encoding glycan modifying enzymes (glycosyltransferase and glycosidase) and/or genes involved in the metabolism of substrates of the enzymes in the Hpulg3Δ or Hpoch2Δalg3Δ double-deficient mutant strain of the present invention.

In order to create complex glycan structures such as a human hybrid type or complex type, manipulation to add specific sugars may be performed. For example, sugars commonly found in human glycoproteins, such as sialic acid, galactose, and fucose, are generally lacking in the yeast system. Sialic acid galactose, fucose, and the like may be added to glycoproteins using one or more genes encoding glycosyltransferases and genes involved in the metabolism of their substrates, thereby producing various human-type glycoproteins which are similar to those of human cells.

A produced glycoprotein may be purified by an ordinary method, and the purification protocol may be determined according to the properties of the specific protein to be purified. This determination is considered an ordinary skill to those skilled in the art. For example, a target protein may be purified by atypical isolation technique, such as precipitation, immunoadsorption, fractionization or various chromatographic methods.

Glycoproteins capable of being produced according to the present invention are exemplified by cytokines (e.g., EPO, interferon-α, interferonβ, interferon-γ, G-CSF. etc.), clotting factors (e.g., VIII factor, IX factor, human protein C), antibodies for therapeutic use (e.g., immunogoblulins, Fab, double specific antibodies, monovalent antibodies, diabody, etc.) and Fc fusion proteins, therapeutic enzymes (e.g., glucocerebrosidase, α-galactosidase, α-L-iduronidase, α-glucosidase, etc.), endothelial growth factor, growth homione releasing factor, *Typanosoma cruzi* trans-sialidase, HIV envelope protein, influenza virus A haemagglutinin, influenza neuraminidase, bovine enterokinase activator, bovine herpes virus type-1 glycoprotein D, human angiostatin, human B7-1, B7-2 and B-7 receptor CTLA-4, human tissue factor, growth factors (e.g., platelet-derived growth factor), human α-antitrypsin, tissue plasminogen activator, plasminogen activator inhibitor-1, urokinase, plasminogen, and thrombin.

In still another aspect, the present invention relates to various human-derived glycoproteins prepared using the *H. polymorpha* mutant strain of the present invention.

Since glycoproteins prepared according to the present process, which have human-type glycans, are less immunogenic in humans, and are identical or similar to proteins produced in humans with respect to solubility, sensitivity to proteases, trafficking, transport, secretion, recognition by other proteins or factors, and the like, they may be suitable for therapeutic and/or diagnostic uses.

A better understanding of the present invention may be obtained through the following examples which are set forth to illustrate, but are not to be construed as the limit of the present invention.

EXAMPLE 1

Obtainment and Amino Acid Sequence Analysis of *Hansenula polymorpha* ALG3 Gene

A polymerase chain reaction (PCR) was carried out using chromosomal DNA, which was extracted from *H. polymorpha* DL-1 strain (Levine and Cooney, Appl. Microbiol., 26, 982-990, (1973)), as a template and a pair of primers (AL3-N and AL3-C, Table 1). As a result, an obtained DNA fragment of 1.36 kb was sequenced, and subjected to amino acid sequence analysis.

Figure 2:
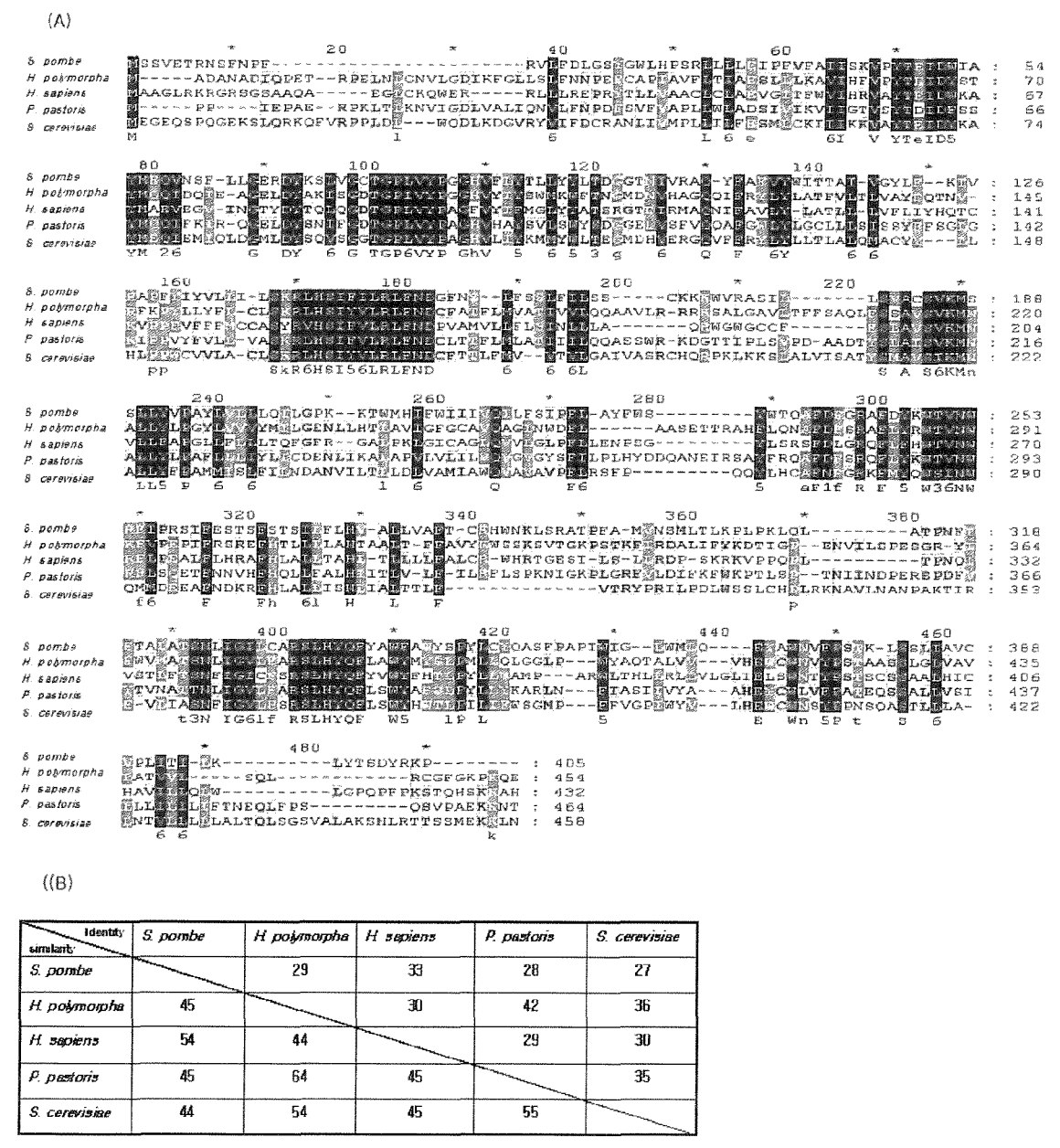

An open reading frame designated as HpALG3, is found to be 1,362 by in size and encodes a protein consisting of 454 amino acid residues. The HpAlg3 protein had four putative transmembrane spanning regions on its amino acid sequence, and was thus considered to be a membrane protein (FIG. 1). In FIG. 1, the four putative transmembrane spanning regions are underlined at amino acid residues from 42 to 58, from 176 to 192, from 221 to 237, and from 425 to 441. The HpAlg3 protein exhibited a 30% identity and a 44% similarity with human (*Homo sapiens*) Alg3 protein, and also had the following identities and similarities with other yeasts: 36% identity and 54% similarity with *Saccharomyces cerevisiae*, 29% identity and 45% similarity with *Schizosaccharomyces pombe*, and 42% identity and 64% similarity with *Pichia pastoris*. The HpAlg3 protein was found to be closest to the Alg3 protein of *P. pastoris* (FIG. 2).

TABLE 1

| Primer | Sequences |
|---|---|
| AL3-N | 5'-ATGGCAGATGCAAATGCGG-3' |
| AL3-C | 5'-TTATTCCTGTTTGGGTTTGCCG-3' |
| AL3N-S | 5'-GTGTCGCTGCTCAACCCGGA-3' |
| AL3N-A | 5'-AGCTCGGTACCCGGGGATCCTGCCATCTCGTACGCTCGTG-3' |
| AL3C-S | 5'-GCACATCCCCCTTTCGCCAGGTCGCAGCTCCGGTGTGGCT-3' |
| AL3C-A | 5'-GACGGCCGTCGAGTCCGACA-3' |
| UN-S | 5'-GGATCCCCGGGTACCGAGCT-3' |
| UN-A | 5'-CACCGGTAGCTAATGATCCC-3' |
| UC-S | 5'-CGAACATCCAAGTGGGCCGA-3' |
| UC-A | 5'-CTGGCGAAAGGGGGATGTGC-3' |

EXAMPLE 2

Figure 4:
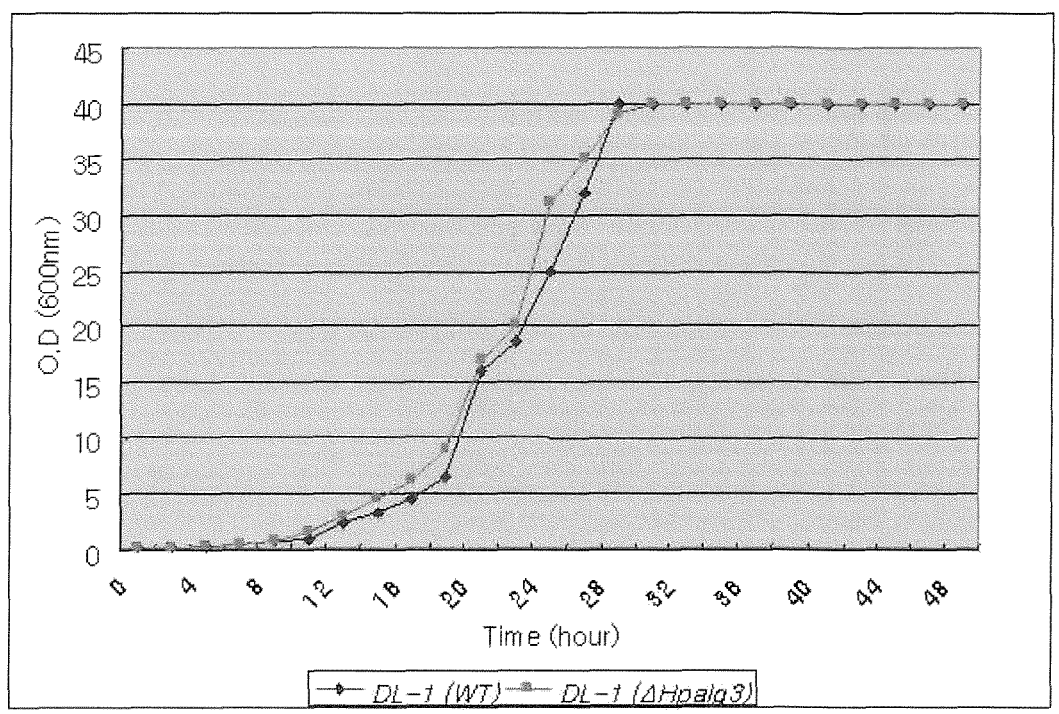
FIG. 4 is a graph showing growth properties of an *H. polymorpha* ALG3 deletion mutant strain (Hpalg3 Δ) and its wild type, wherein cultivation was carried out with YPD broth (1% yeast extract, 2% Bacto-peptone, 2% dextrose) at 37° C. with agitation.
Figure 5:
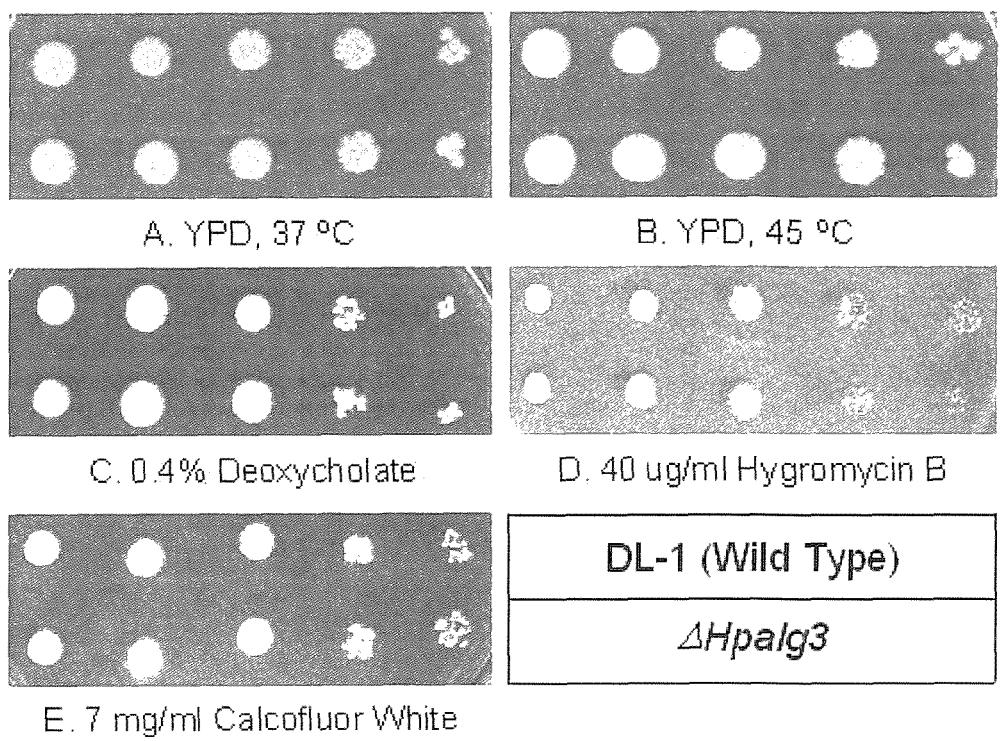
FIG. 5 shows the growth properties of an Hpalg3 Δ mutant strain. Cultures of an *H. polymorpha* wild type and the Hpalg3Δ mutant strain, which had reached an exponential growth phase ($OD_{600}$=1), were 10-fold serially diluted, and 3 μl of each dilution was spotted on a designated agar plate and incubated further for two days (A: YPD medium at 37° C.; B: YPD medium at 45° C.; C: YPD medium supplemented with 0.4% sodium deoxycholate; D: YPD medium supplemented with 40 μg/ml hygromyeine B; E: YPD medium supplemented with 7 mg/ml Calcofluor white; all plates except for B were incubated at 37° C.)

Construction of HpALG3 Gene-Deficient Strain and Analysis of Characteristics of the Strain In order to construct a mutant strain disrupted in the HpALG3 gene, gene disruption was performed by a combination of fusion PCR with the primers (primers used in PCR for cloning and disruption of the HpALG3 gene) listed in Table 1 and in vivo homologous recombination (Oldenburg et al., Nucleic Acid Res., 25, 451, (1997)). Primary PCR were carried out with four pairs of primers to amplify 5'-end and 3'-end regions of the URA3 gene (UN-S and UN-A primers for 5'-end region, UC-S and UC-A primers for 3'-end region) and the HpALG3 gene (AL3N-S and AL3N-A primers for 5'-end fragment, AL3C-S and AL3C-A primers for 3'-end fragment). Secondary fusion PCR were then carried out to link the 5'-end fragment of the HpALG3 gene to the 5' region of the URA3 gene (using a pair of AL3N-S and UN-A primers) and to link the 3' region of the URA3 gene to the 3'-end fragment of the HpALG3 gene (using a pair of UC-S and AL3C-A primers). Then, the resulting two DNA fragments were introduced into yeast cells, and transformants in which the HpALG3 gene was disrupted by in vivo recombination were selected (FIG. 3). Primarily, using an URA3 selection marker, transformants grown in a minimum medium lacking uracil were selected. Then, amplified DNA fragments produced by PCR were examined to verify whether they differed from those of a wild-type strain, thereby selecting an *H. polymorpha* mutant strain with the deletion of HpALG3, Hpalg3Δ (leu2; alg3:: URA3). The Hpalg3Δ mutant strain, deleted in the HpALG3 gene, was deposited at KCTC (Korean Collection for Type Cultures; KRIBB, 52, Oun-dong, Yusong-ku, Taejon, Korea) on Oct. 27, 2005, and assigned accession number KCTC 10867BP. The obtained Hpalg3Δ strain was evaluated for growth properties. The Hpalg3Δ strain did not exhibit growth inhibition caused by the sensitivity to temperature, antibiotics such as hygromycin B, calcofluor white and sodium deoxycholate, such growth inhibition being common in yeast mutant strains having a defect in oligosaccharide chain synthesis (FIGS. 4 and 5). Conclusively, the Hpalg3Δ strain had growth properties similar to those of the wild type.

EXAMPLE 3

Figure 6:
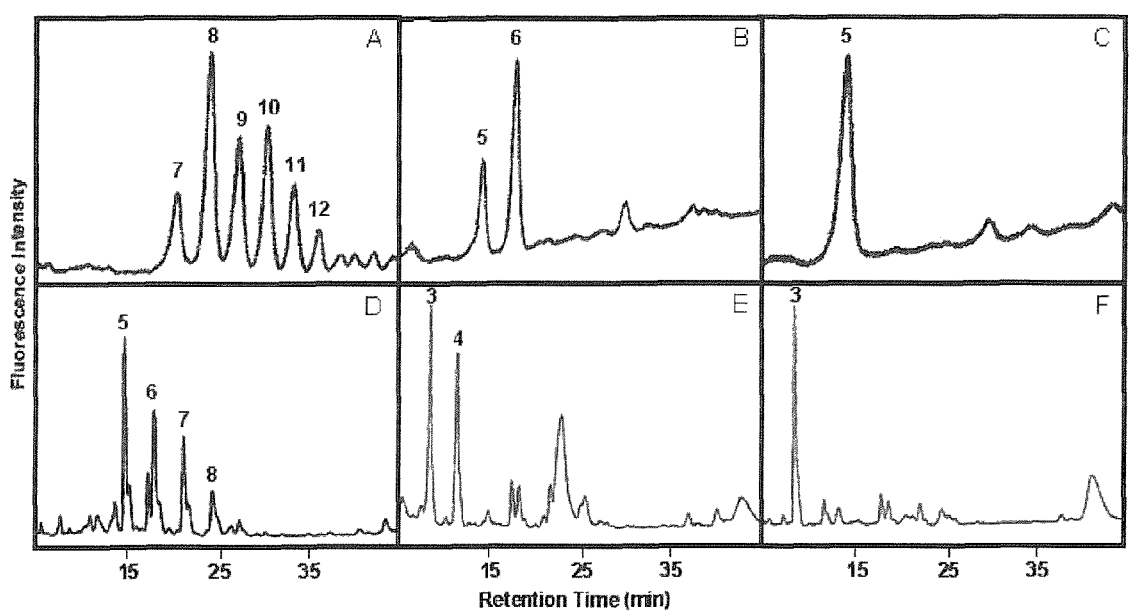
FIG. 6 shows the results of HPLC analysis elucidating the structures of glycans attached to the Ypsl protein expressed in *H. polymorpha* wild-type and mutant strains (panels A and D: glycan profiles of the Ypsl protein secreted from *H. polymorpha* wild-type and Hpalg3 Δ mutant strains, respectively; panels B and E: their glycan profiles after the treatment with exogenously added α-1,2-mannosidase; panels C and F: their glycan profiles after treatment with exogenously added α-1,2-mannosidase and α-1,6-mannosidase)

Structural Analysis of N-Glycans Assembled on a Glycoprotein Produced from the Hpalg3Δ Mutant To analyze the N-glycan structures of a glycoprotein synthesized in the Hpalg3Δ mutant prepared in Example 2, an *H. polymorpha* glycoprotein, yapsin 1 (Yps1p), was expressed in a secreted form in the *H. polymorpha* wild-type and Hpalg3Δ mutant strains. The glycoprotein, Yps1p, has four putative amino acid sequences for N-linked glycosylation. The *H. polymorpha* wild-type and Hpalg3Δ mutant strains were individually transformed with a pDLMOX-YPSI(H) vector expressing Yps1p tagged with six-histidine residues under the MOX promoter (Y J Kim, Biosynthesis and Maturation of Yapsins in the Methylotropic Yeast *Hansenula polymorpha*, master's thesis, National Chungnam University, Korea (2005)). The transformants were grown in YPD medium and transferred to YPM medium (1% yeast extract, 2% Bacto-peptone, 2% methanol) to induce the expression of Yps1p. The collected culture medium, which contains secreted Yps1p protein, was passed through a nickel column to selectively isolate only Yps1p tagged with six histidines at the C-terminal end. The isolated recombinant his-tagged Yps1p was treated with PNGase F to detach attached glycans therefrom. Then, the released glycans were labelled with 2-aminopyridine (2-PA) and subjected to HPLC analysis. As shown in panel A of FIG. 6, oligosaccharides attached to the wild type-derived Yps1p were found to have various size distributions ranging from 7 to 12 mannose residues ($Man_{7-12}GlcNAc_2$). In contrast, oligosaccharides profile of Hpalg3Δ-derived Yps1p (panel D of FIG. 6) showed that the major peak of $Man_5GlcNAc_2$ containing 5 mannose residues was detected together with smaller peaks of oligosaccharides ($Man_{6-8}GlcNAc_2$) containing 6 to 8 mannose residues. The oligosaccharides containing 2 to 4 fewer mannose residues in the Hpalg3Δ mutant strain than in the wild-type strain are considered to result from the loss of dolichyl-phosphate-mannose dependent α-1,3-mannosyltransferase activity by disrupting the HpALG3 gene. It means that the elaboration process of dolichyl phosphate-linked oligosaccharide is blocked at the initial marmosylation step mediated by HpAlg3 protein. Therefore, $Glc_3Man_5GlcNAc_2$ instead of $Glc_3Man_9GlcNAc_2$, might be transferred to nascent proteins and the resulting glycoproteins can be further processed in ER and Golgi.

The oligosaccharides released from Yps1p were further analyzed by the sequential treatment of α-1,2-mannosidase and α-1,6-mannosidase to investigate their profiles and linkages in detail. The panel B of FIG. 6 indicates that the oligosaccharides synthesized in the wild-type strain were converted to oligonucleotides Nan$_{5-6}$GlcNAc$_2$) consisting of five or six mannose residues after α-1,2-mannosidase treatment. All of them were then converted to oligosaccharides consisting of five mannose residues by α-1,6-mannosidase treatment (panel C, FIG. 6). In contrast, oligosaccharides synthesized in the Hpalg3Δ mutant strain were converted to oligonucleotides (Man$_{3-4}$GlcNAc$_2$) containing three or four mannose residues after α-1,2-mannosidase treatment (panel E, FIG. 6), and all of them were then converted to the trimannose core oligosaccharide (Man$_3$GlcNAc$_2$) containing three mannose residues by α-1,6-mannosidase treatment (panel F, FIG. 6). This trimannose core oligosaccharide is the minimal core backbone of human-type glycans which can be converted to various human glycans after the successive addition of N-acetylglucosamine, galactose and sialic acid. Taken together, since the HpALG3 gene product has dolichyl-phosphate-mannose dependent α-1,3-mannosyltransferase activity, and the Hpalg3Δ mutant strain is blocked in the early stage of the lipid-linked oligosaccharide biosynthesis, the present mutant strain is useful in the synthesis of the trimannose core oligosaccharide, which is the minimal core backbone of human-type glycans.

EXAMPLE 4

Glycoengineering Using *H. polymorpha* Hpoch2Δalg3Δ Double-Deficient Mutant Strain The present inventors, prior to the present invention, successfully restricted the yeast-specific outer chain synthesis in the glycosylation process of *H. polymorpha* using a mutant strain deficient in the HpOCH2 gene encoding α-1,6-mannosyltransferase (Korean Pat. Application No. 2004-6352; PCT Application PCT/KR2004/001819). The present inventors constructed a thither improved mutant strain, that is, an *H. polymorpha* Hpoch2Δalg3Δ double-deficient mutant strain, by disrupting the dolichyl-phosphate-mannose dependent α-1,3-mannosyltransferase gene in the HpOCH2 gene-deficient mutant strain as a parent strain using fusion PCR and in vivo DNA recombination, which are described in Example 2. The *H. polymorpha* Hpoch2Δalg3Δ mutant strain, deleted in both HpALG3 and HpOCH2 genes, was deposited at KCTC (Korean Collection for Type Cultures; KRIBB, 52, Oun-dong, Yusong-ku, Taejon, Korea) on Oct. 27, 2005, and assigned accession number KCTC 10868BP. Thereafter, according to the method described in Example 3, the yapsin 1 gene was introduced to express the Yps1p protein in a secreted form, the Yps1p protein was purified, and oligosaccharides released from the proteins were recovered, fluorescent-labeled, and subjected to HPLC analysis. Oligosaccharides of the wild-type strain were found to contain 7 to 12 mannose residues (panel A, FIG. 7). In contrast, a glycoprotein synthesized in the Hpoch2Δalg3Δ double-deficient mutant strain had oligosaccharides remarkably reduced in length (Man$_{4-6}$GlcNAc$_2$), containing 4, 5 and 6 mannose residues (panel B, FIG. 7).

Figure 7:
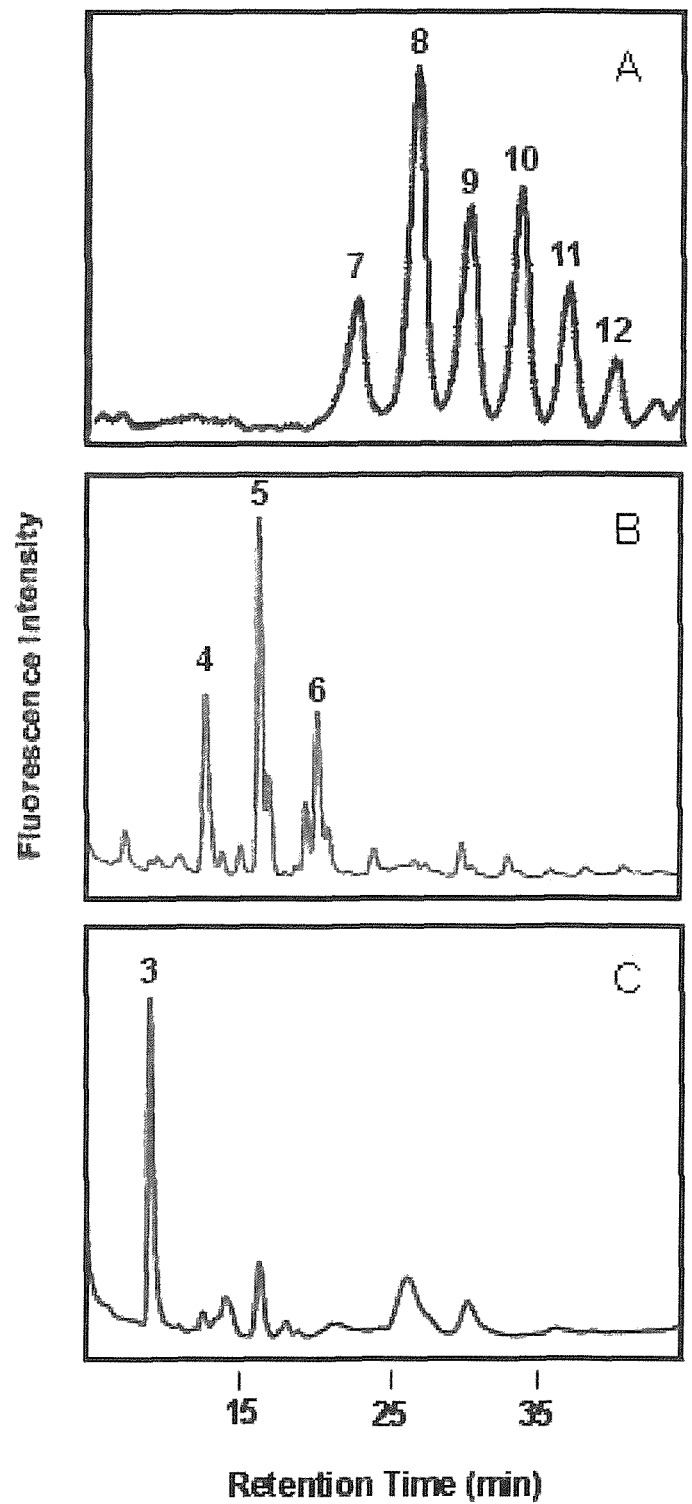
FIG. 7 shows the results of HPLC analysis elucidating glycan structures of a glycoprotein produced from Hpoch2Δalg3Δ double-deficient mutant strain and a glycoengineered strain thereof (A: glycan profiles of *H. polymorpha* wild-type strain; B: glycan profiles of Hpoch2Δalg3Δdouble-deficient mutant strain; C: glycan profiles of a recombinant mutant strain engineered with the ER-targeting expression of *Aspergillus saitoi* α-1,2-mannosidase (MsdS) in the *H. polymorpha* double deletion background (Hpoch2Δalg3Δ)).

In addition, in order to obtain an *H. polymorpha* strain synthesizing the trimannose core oligosaccharide, which is the minimal common backbone for all human-type N-glycan biosynthesis, the present inventors employed a method of expressing *A. saitoi* α-1,2-mannosidase in the ER of *H. polymorpha*, the method being described in a previous study (Chiba et al., J. Biol. Chem., 273, 26298-26304, (1998)) carried out with the traditional yeast *S. cerevisiae*. The Hpoch2Δalg3Δ double-deficient mutant strain was transformed with a vector carrying the α-1,2-mannosidase gene expression cassette, pDUMOX-MsdS(HA-HDEL), (Kim et al. J. Biol. Chem. 281, 6261-6272 (2006)), thereby yielding a glycoengineered recombinant strain, Hpoch2Δalg3Δ-MsdSp. In order to determine whether the glycoengineered *H. polymorpha* strain (Hpoch2Δalg3Δ-MsdSp) actually synthesizes the trimannose core oligosaccharide (Man$_3$GlcNAc$_2$), the recombinant HpYps1p protein was expressed in the Hpoch2Δalg3Δ-MsdSp strain and its oligosaccharide profile was then analyzed according to the method described in Example 3. Panel C of FIG. 7 shows that the glycoengineered recombinant strain mostly synthesize the trimannose core oligosaccharide (Man$_3$GlcNAc$_2$) containing three mannose residues. Since it is the minimal core backbone for human-type glycoprotein production, the present strain may be applied usefully in glycoengineering for human-type oligosaccharide-attached glycoproteins.

INDUSTRIAL APPLICABILITY

The high value-added recombinant therapeutic glycoproteins are leading the biologics market, and there is thus a rapid increase in market demand for expression systems for producing high quality therapeutic glycoproteins at high efficiency. Since the methylotrophic yeast *H. polymorpha* has been approved worldwide as a host system for the mass production of recombinant hepatitis B vaccines, it is highlighted as preferable recombinant protein expression system for recombinant protein therapeutics. However, *H. polymorpha* has not been widely used especially for therapeutic glycoproteins due to its yeast-specific high-mannose oligosaccharide structure. As described in the above Examples, the present invention showed that the Hpalg3Δ mutant strain deficient in the HpALG3 gene and the Hpoch2Δalg3Δ double-deficient mutant strain synthesized oligosaccharides having remarkably reduced mannose residues. Moreover, the oligosaccharides can be readily converted to the trimannose core oligosaccharide (Man$_3$GlcNAc$_2$), which is the minimal backbone of human-type oligosaccharides, through α-1,2-mannosidase expression. Thus, the above mutants or mutants having a remodeled oligosaccharide modification process enable the production of glycoproteins in a form having glycan structures closer to human hybrid-type and complex-type glycan structures compared to wild-type yeast strains. That is, the present invention provides versatile *H. polymorpha* systems capable of mass producing high quality therapeutic glycoproteins at high efficiency by developing a fundamental host to be designed for the production of human-derived therapeutic glycoproteins.

We claim:

1. A method for preparing a glycoprotein with human-type N-glycans, comprising the steps of:
   (a) introducing a target gene encoding a protein of interest into the *Hansenula polymorpha* mutant strain which is Hpalg3 Δ deposited under accession number KCTC 10867BP or Hpoch2 Δalg3 Δ deposited under accession number KCTC 10868BP to prepare a transformant;
   (b) culturing the transformant to induce the expression of the target protein in a secreted form; and
   (c) purifying the target protein expressed and secreted by the transformant,
   wherein the target protein purified in step (c) has a human-type N-glycan structure containing 3 to 8 mannose residues.

2. The method of claim 1, wherein the target protein purified in step (c) has a human-type N-glycan structure containing 5 to 8 mannose residues.

3. The method of claim 1, wherein the target protein purified in step (c) has a human-type N-glycan structure containing 4 to 6 mannose residues.

4. The method of claim 1, wherein the target protein purified in step (c) has a human-type N-glycan structure containing 3 mannose residues.

5. The method of claim 1, further comprising a step of treating the target protein purified in step (c) with α-1,2-mannosidase and α-1,6-mannosidase successively.

* * * * *

SEQUENCE LISTING

```
<160> NUMBER OF SEQ ID NOS: 17

<210> SEQ ID NO 1
<211> LENGTH: 1362
<212> TYPE: DNA
<213> ORGANISM: Hansenula polymorpha
<220> FEATURE:
```

```
<221> NAME/KEY: CDS
<222> LOCATION: (1)..(1362)
<223> OTHER INFORMATION: alpha-1,3-mannosyltransferase

<400> SEQUENCE: 1 atg gca gat gca aat gcg gat ata cag ccc gaa aca cgg ccg gag ctc         48
Met Ala Asp Ala Asn Ala Asp Ile Gln Pro Glu Thr Arg Pro Glu Leu
 1               5                  10                  15 aac tta gga aat gtc ctg ggc gat atc aag ttt gga ttg ttg tcg ctg         96
Asn Leu Gly Asn Val Leu Gly Asp Ile Lys Phe Gly Leu Leu Ser Leu
            20                  25                  30 ttc aac aac cct gag ttc tgc gcg cca atc gcc gtc ttt ctg acc atc        144
Phe Asn Asn Pro Glu Phe Cys Ala Pro Ile Ala Val Phe Leu Thr Ile
        35                  40                  45 gca gag tcg ctt ctc ctc aag gcc gtg atc cat ttt gtc ccc tac acc        192
Ala Glu Ser Leu Leu Leu Lys Ala Val Ile His Phe Val Pro Tyr Thr
 50                  55                  60 gag att gac tac agc acg tac atg cag cag atc gac caa att gag gct        240
Glu Ile Asp Tyr Ser Thr Tyr Met Gln Gln Ile Asp Gln Ile Glu Ala
 65                  70                  75                  80 gga gag ctt gac tac gcc aaa att agc ggc gac aca ggc cca att gtg        288
Gly Glu Leu Asp Tyr Ala Lys Ile Ser Gly Asp Thr Gly Pro Ile Val
                85                  90                  95 tat ccc ggc gga cat gtc tac ata tac tcg tgg atg aag tgg ttc acc        336
Tyr Pro Gly Gly His Val Tyr Ile Tyr Ser Trp Met Lys Trp Phe Thr
           100                 105                 110 aac ggg atg gac aac gtg cac gct ggc cag cag att ttc agg tat cta        384
Asn Gly Met Asp Asn Val His Ala Gly Gln Gln Ile Phe Arg Tyr Leu
       115                 120                 125 tat ctg gcg aca ttt gtg cta act ctg gtt gcg tat ttc cag aca aat        432
Tyr Leu Ala Thr Phe Val Leu Thr Leu Val Ala Tyr Phe Gln Thr Asn
   130                 135                 140 gtg cgg ttc aag ccg tac ctg ctc tac ttt ctg tgt ctg tcc aaa cgg        480
Val Arg Phe Lys Pro Tyr Leu Leu Tyr Phe Leu Cys Leu Ser Lys Arg
145                 150                 155                 160 ttg cac tcc atc tac gtg ctg cgg ctg ttc aac gac tgc ttt gcc acg        528
Leu His Ser Ile Tyr Val Leu Arg Leu Phe Asn Asp Cys Phe Ala Thr
                165                 170                 175 ttt ctg atg gtg gct acg atc gtc gtt ctg cag cag gct gcc gtt ttg        576
Phe Leu Met Val Ala Thr Ile Val Val Leu Gln Gln Ala Ala Val Leu
            180                 185                 190 cgg cgc agg aag agc gct ctg ggc gca gtg ctc acc ttt ttc agc gca        624
Arg Arg Arg Lys Ser Ala Leu Gly Ala Val Leu Thr Phe Phe Ser Ala
        195                 200                 205 cag ttg ttc agc tcc gcc gtc agc gtt aag atg aac gct ctg ctg tat        672
Gln Leu Phe Ser Ser Ala Val Ser Val Lys Met Asn Ala Leu Leu Tyr
    210                 215                 220 ctg ccg ggc tac ttg gtg gtg gtg tac atg atc ctg gga gaa aac ctg        720
Leu Pro Gly Tyr Leu Val Val Val Tyr Met Ile Leu Gly Glu Asn Leu
225                 230                 235                 240 ctg cac acg ctt gcc gtg att ggt ttc ggg tgt gca gtg cag gca ggc        768
Leu His Thr Leu Ala Val Ile Gly Phe Gly Cys Ala Val Gln Ala Gly
                245                 250                 255 att aac tgg gac ttc ctg gcg gcc tcg gag acc aca aga gca cat ttc        816
Ile Asn Trp Asp Phe Leu Ala Ala Ser Glu Thr Thr Arg Ala His Phe
            260                 265                 270 ctg cag aac gct ttc gac ttc agc cgt gct ttt ctg tac cgc tgg acg        864
Leu Gln Asn Ala Phe Asp Phe Ser Arg Ala Phe Leu Tyr Arg Trp Thr
        275                 280                 285 gtc aac tgg aag ttt gtg ccg gag ccc att ttc cgc agc cgc gag ttc        912
Val Asn Trp Lys Phe Val Pro Glu Pro Ile Phe Arg Ser Arg Glu Phe
```

```
                  290                 295                 300
cac acg ttg ctg ctg ctg gcg cac aca gcc gca ctg acg ttt ttc gcg         960
His Thr Leu Leu Leu Leu Ala His Thr Ala Ala Leu Thr Phe Phe Ala
305                 310                 315                 320 gtg tac aaa tgg agc agt aaa tct gtc acg gga aaa cca tcc acc aaa        1008
Val Tyr Lys Trp Ser Ser Lys Ser Val Thr Gly Lys Pro Ser Thr Lys
                    325                 330                 335 ttt atc aga gac gca ctg att ttc tac aaa gac acc ata ggc cca gaa        1056
Phe Ile Arg Asp Ala Leu Ile Phe Tyr Lys Asp Thr Ile Gly Pro Glu
                340                 345                 350 aat gtg ata ctc tcc cca gaa agc ggc aga tac atc ttc tgg gtg atg        1104
Asn Val Ile Leu Ser Pro Glu Ser Gly Arg Tyr Ile Phe Trp Val Met
            355                 360                 365 gcg acg tcg aac ttg atc ggc gtc ttg ttc gcg cgc tcg ctg cac tac        1152
Ala Thr Ser Asn Leu Ile Gly Val Leu Phe Ala Arg Ser Leu His Tyr
        370                 375                 380 cag ttc ttg gcc tgg tat atg tac tcg ctg cca atg ctg ctg cag ctg        1200
Gln Phe Leu Ala Trp Tyr Met Tyr Ser Leu Pro Met Leu Leu Gln Leu
385                 390                 395                 400 ggc ggg ctg ccg tgg tac gca cag acg gcg ctc gtg gtg gtc cac gag        1248
Gly Gly Leu Pro Trp Tyr Ala Gln Thr Ala Leu Val Val Val His Glu
                    405                 410                 415 tgg tgc tgg aac gtg tac ccc agc aca gcg gcc agc tcg ttg ggc ctg        1296
Trp Cys Trp Asn Val Tyr Pro Ser Thr Ala Ala Ser Ser Leu Gly Leu
                420                 425                 430 gtg gca gtg ctt gcg aca gtg gtt ttg tcg cag ctc cgg tgt ggc ttc        1344
Val Ala Val Leu Ala Thr Val Val Leu Ser Gln Leu Arg Cys Gly Phe
            435                 440                 445 ggc aaa ccc aaa cag gaa                                                 1362
Gly Lys Pro Lys Gln Glu
    450

<210> SEQ ID NO 2
<211> LENGTH: 454
<212> TYPE: PRT
<213> ORGANISM: Hansenula polymorpha

<400> SEQUENCE: 2

Met Ala Asp Ala Asn Ala Asp Ile Gln Pro Glu Thr Arg Pro Glu Leu
1               5                   10                  15

Asn Leu Gly Asn Val Leu Gly Asp Ile Lys Phe Gly Leu Leu Ser Leu
                20                  25                  30

Phe Asn Asn Pro Glu Phe Cys Ala Pro Ile Ala Val Phe Leu Thr Ile
            35                  40                  45

Ala Glu Ser Leu Leu Leu Lys Ala Val Ile His Phe Val Pro Tyr Thr
        50                  55                  60

Glu Ile Asp Tyr Ser Thr Tyr Met Gln Gln Ile Asp Gln Ile Glu Ala
65                  70                  75                  80

Gly Glu Leu Asp Tyr Ala Lys Ile Ser Gly Asp Thr Gly Pro Ile Val
                    85                  90                  95

Tyr Pro Gly Gly His Val Tyr Ile Tyr Ser Trp Met Lys Trp Phe Thr
                100                 105                 110

Asn Gly Met Asp Asn Val His Ala Gly Gln Gln Ile Phe Arg Tyr Leu
            115                 120                 125

Tyr Leu Ala Thr Phe Val Leu Thr Leu Val Ala Tyr Phe Gln Thr Asn
        130                 135                 140

Val Arg Phe Lys Pro Tyr Leu Leu Tyr Phe Leu Cys Leu Ser Lys Arg
145                 150                 155                 160
```

```
Leu His Ser Ile Tyr Val Leu Arg Leu Phe Asn Asp Cys Phe Ala Thr
            165                 170                 175

Phe Leu Met Val Ala Thr Ile Val Val Leu Gln Gln Ala Ala Val Leu
            180                 185                 190

Arg Arg Arg Lys Ser Ala Leu Gly Ala Val Leu Thr Phe Phe Ser Ala
            195                 200                 205

Gln Leu Phe Ser Ser Ala Val Ser Val Lys Met Asn Ala Leu Leu Tyr
            210                 215                 220

Leu Pro Gly Tyr Leu Val Val Tyr Met Ile Leu Gly Glu Asn Leu
225                 230                 235                 240

Leu His Thr Leu Ala Val Ile Gly Phe Gly Cys Ala Val Gln Ala Gly
            245                 250                 255

Ile Asn Trp Asp Phe Leu Ala Ala Ser Glu Thr Thr Arg Ala His Phe
            260                 265                 270

Leu Gln Asn Ala Phe Asp Phe Ser Arg Ala Phe Leu Tyr Arg Trp Thr
            275                 280                 285

Val Asn Trp Lys Phe Val Pro Glu Pro Ile Phe Arg Ser Arg Glu Phe
            290                 295                 300

His Thr Leu Leu Leu Ala His Thr Ala Leu Thr Phe Phe Ala
305                 310                 315                 320

Val Tyr Lys Trp Ser Ser Lys Ser Val Thr Gly Lys Pro Ser Thr Lys
            325                 330                 335

Phe Ile Arg Asp Ala Leu Ile Phe Tyr Lys Asp Thr Ile Gly Pro Glu
            340                 345                 350

Asn Val Ile Leu Ser Pro Glu Ser Gly Arg Tyr Ile Phe Trp Val Met
            355                 360                 365

Ala Thr Ser Asn Leu Ile Gly Val Leu Phe Ala Arg Ser Leu His Tyr
            370                 375                 380

Gln Phe Leu Ala Trp Tyr Met Tyr Ser Leu Pro Met Leu Leu Gln Leu
385                 390                 395                 400

Gly Gly Leu Pro Trp Tyr Ala Gln Thr Ala Leu Val Val Val His Glu
            405                 410                 415

Trp Cys Trp Asn Val Tyr Pro Ser Thr Ala Ala Ser Ser Leu Gly Leu
            420                 425                 430

Val Ala Val Leu Ala Thr Val Val Leu Ser Gln Leu Arg Cys Gly Phe
            435                 440                 445

Gly Lys Pro Lys Gln Glu
            450
```

<210> SEQ ID NO 3
<211> LENGTH: 19
<212> TYPE: DNA
<213> ORGANISM: Artificial Sequence
<220> FEATURE:
<223> OTHER INFORMATION: primer AL3-N

<400> SEQUENCE: 3
atggcagatg caaatgcgg                                             19

<210> SEQ ID NO 4
<211> LENGTH: 22
<212> TYPE: DNA
<213> ORGANISM: Artificial Sequence
<220> FEATURE:
<223> OTHER INFORMATION: primer AL3-C

<400> SEQUENCE: 4
ttattcctgt ttgggtttgc cg                                         22

```
<210> SEQ ID NO 5
<211> LENGTH: 20
<212> TYPE: DNA
<213> ORGANISM: Artificial Sequence
<220> FEATURE:
<223> OTHER INFORMATION: primer AL3N-S

<400> SEQUENCE: 5
gtgtcgctgc tcaacccgga                                              20

<210> SEQ ID NO 6
<211> LENGTH: 40
<212> TYPE: DNA
<213> ORGANISM: Artificial Sequence
<220> FEATURE:
<223> OTHER INFORMATION: primer AL3N-A

<400> SEQUENCE: 6
agctcggtac ccggggatcc tgccatctcg tacgctcgtg                         40

<210> SEQ ID NO 7
<211> LENGTH: 40
<212> TYPE: DNA
<213> ORGANISM: Artificial Sequence
<220> FEATURE:
<223> OTHER INFORMATION: primer AL3C-S

<400> SEQUENCE: 7
gcacatcccc ctttcgccag gtcgcagctc cggtgtggct                         40

<210> SEQ ID NO 8
<211> LENGTH: 20
<212> TYPE: DNA
<213> ORGANISM: Artificial Sequence
<220> FEATURE:
<223> OTHER INFORMATION: primer AL3C-A

<400> SEQUENCE: 8
gacggccgtc gagtccgaca                                              20

<210> SEQ ID NO 9
<211> LENGTH: 20
<212> TYPE: DNA
<213> ORGANISM: Artificial Sequence
<220> FEATURE:
<223> OTHER INFORMATION: primer UN-S

<400> SEQUENCE: 9
ggatccccgg gtaccgagct                                              20

<210> SEQ ID NO 10
<211> LENGTH: 20
<212> TYPE: DNA
<213> ORGANISM: Artificial Sequence
<220> FEATURE:
<223> OTHER INFORMATION: primer UN-A

<400> SEQUENCE: 10
caccggtagc taatgatccc                                              20

<210> SEQ ID NO 11
<211> LENGTH: 20
<212> TYPE: DNA
<213> ORGANISM: Artificial Sequence
<220> FEATURE:
<223> OTHER INFORMATION: primer UC-S
```

<400> SEQUENCE: 11
cgaacatcca agtgggccga         20

<210> SEQ ID NO 12
<211> LENGTH: 20
<212> TYPE: DNA
<213> ORGANISM: Artificial Sequence
<220> FEATURE:
<223> OTHER INFORMATION: primer UC-A

<400> SEQUENCE: 12
ctggcgaaag ggggatgtgc         20

<210> SEQ ID NO 13
<211> LENGTH: 405
<212> TYPE: PRT
<213> ORGANISM: Schizosaccharomyces pombe

<400> SEQUENCE: 13

Met Ser Ser Val Glu Thr Arg Asn Ser Phe Asn Pro Phe Arg Val Leu
1               5                   10                  15

Phe Asp Leu Gly Ser Tyr Gly Trp Leu His Pro Ser Arg Leu Leu Leu
            20                  25                  30

Leu Glu Ile Pro Phe Val Phe Ala Ile Ile Ser Lys Val Pro Tyr Thr
        35                  40                  45

Glu Ile Asp Trp Ile Ala Tyr Met Glu Gln Val Asn Ser Phe Leu Leu
    50                  55                  60

Gly Glu Arg Asp Tyr Lys Ser Leu Val Gly Cys Thr Gly Pro Leu Val
65                  70                  75                  80

Tyr Pro Gly Gly His Val Phe Leu Tyr Thr Leu Tyr Tyr Leu Thr
                85                  90                  95

Asp Gly Gly Thr Asn Ile Val Arg Ala Gln Tyr Phe Ala Phe Val Tyr
            100                 105                 110

Trp Ile Thr Thr Ala Ile Val Gly Tyr Leu Phe Lys Ile Val Arg Ala
        115                 120                 125

Pro Phe Tyr Ile Tyr Val Leu Leu Ile Leu Ser Lys Arg Leu His Ser
    130                 135                 140

Ile Phe Ile Leu Arg Leu Phe Asn Asp Gly Phe Asn Ser Leu Phe Ser
145                 150                 155                 160

Ser Leu Phe Ile Leu Ser Ser Cys Lys Lys Lys Trp Val Arg Ala Ser
                165                 170                 175

Ile Leu Leu Ser Val Ala Cys Ser Val Lys Met Ser Ser Leu Leu Tyr
            180                 185                 190

Val Pro Ala Tyr Leu Val Leu Leu Gln Ile Leu Gly Pro Lys Lys
        195                 200                 205

Thr Trp Met His Ile Phe Trp Ile Ile Val Gln Ile Leu Phe Ser
    210                 215                 220

Ile Pro Phe Leu Ala Tyr Phe Trp Ser Tyr Trp Thr Gln Ala Phe Asp
225                 230                 235                 240

Phe Gly Arg Ala Phe Asp Tyr Lys Trp Thr Val Asn Trp Arg Phe Ile
                245                 250                 255

Pro Arg Ser Ile Phe Glu Ser Ser Phe Ser Thr Ser Ile Leu Phe
            260                 265                 270

Leu His Val Ala Leu Leu Val Ala Phe Thr Cys Lys His Trp Asn Lys
        275                 280                 285

Leu Ser Arg Ala Thr Pro Phe Ala Met Val Asn Ser Met Leu Thr Leu

```
            290                 295                 300
Lys Pro Leu Pro Lys Leu Gln Leu Ala Thr Pro Asn Phe Ile Phe Thr
305                 310                 315                 320

Ala Leu Ala Thr Ser Asn Leu Ile Gly Ile Leu Cys Ala Arg Ser Leu
                325                 330                 335

His Tyr Gln Phe Tyr Ala Trp Phe Ala Trp Tyr Ser Pro Tyr Leu Cys
                340                 345                 350

Tyr Gln Ala Ser Phe Pro Ala Pro Ile Trp Ile Gly Leu Trp Met Leu
                355                 360                 365

Gln Glu Tyr Ala Trp Asn Val Phe Pro Ser Thr Lys Leu Ser Ser Leu
                370                 375                 380

Ile Ala Val Cys Val Pro Leu Ile Thr Ile Leu Lys Leu Tyr Thr Ser
385                 390                 395                 400

Asp Tyr Arg Lys Pro
                405

<210> SEQ ID NO 14
<211> LENGTH: 454
<212> TYPE: PRT
<213> ORGANISM: Hansenula polymorpha

<400> SEQUENCE: 14

Met Ala Asp Ala Asn Ala Asp Ile Gln Pro Glu Thr Arg Pro Glu Leu
1               5                   10                  15

Asn Leu Gly Asn Val Leu Gly Asp Ile Lys Phe Gly Leu Leu Ser Leu
                20                  25                  30

Phe Asn Asn Pro Glu Phe Cys Ala Pro Ile Ala Val Phe Leu Thr Ile
            35                  40                  45

Ala Glu Ser Leu Leu Leu Lys Ala Val Ile His Phe Val Pro Tyr Thr
        50                  55                  60

Glu Ile Asp Tyr Ser Thr Tyr Met Gln Gln Ile Asp Gln Ile Glu Ala
65              70                  75                  80

Gly Glu Leu Asp Tyr Ala Lys Ile Ser Gly Asp Thr Gly Pro Ile Val
                85                  90                  95

Tyr Pro Gly Gly His Val Tyr Ile Tyr Ser Trp Met Lys Trp Phe Thr
            100                 105                 110

Asn Gly Met Asp Asn Val His Ala Gly Gln Gln Ile Phe Arg Tyr Leu
        115                 120                 125

Tyr Leu Ala Thr Phe Val Leu Thr Leu Val Ala Tyr Phe Gln Thr Asn
130             135                 140

Val Arg Phe Lys Pro Tyr Leu Leu Tyr Phe Leu Cys Leu Ser Lys Arg
145                 150                 155                 160

Leu His Ser Ile Tyr Val Leu Arg Leu Phe Asn Asp Cys Phe Ala Thr
                165                 170                 175

Phe Leu Met Val Ala Thr Ile Val Leu Gln Gln Ala Ala Val Leu
            180                 185                 190

Arg Arg Arg Lys Ser Ala Leu Gly Ala Val Leu Thr Phe Phe Ser Ala
        195                 200                 205

Gln Leu Phe Ser Ser Ala Val Ser Val Lys Met Asn Ala Leu Leu Tyr
210             215                 220

Leu Pro Gly Tyr Leu Val Val Val Tyr Met Ile Leu Gly Glu Asn Leu
225                 230                 235                 240

Leu His Thr Leu Ala Val Ile Gly Phe Gly Cys Ala Val Gln Ala Gly
                245                 250                 255

Ile Asn Trp Asp Phe Leu Ala Ala Ser Glu Thr Thr Arg Ala His Phe
```

```
                      260                 265                 270
Leu Gln Asn Ala Phe Asp Phe Ser Arg Ala Phe Leu Tyr Arg Trp Thr
                275                 280                 285
Val Asn Trp Lys Phe Val Pro Glu Pro Ile Phe Arg Ser Arg Glu Phe
        290                 295                 300
His Thr Leu Leu Leu Leu Ala His Thr Ala Ala Leu Thr Phe Phe Ala
305                 310                 315                 320
Val Tyr Lys Trp Ser Ser Lys Ser Val Thr Gly Lys Pro Ser Thr Lys
                325                 330                 335
Phe Ile Arg Asp Ala Leu Ile Phe Tyr Lys Asp Thr Ile Gly Pro Glu
            340                 345                 350
Asn Val Ile Leu Ser Pro Glu Ser Gly Arg Tyr Ile Phe Trp Val Met
                355                 360                 365
Ala Thr Ser Asn Leu Ile Gly Val Leu Phe Ala Arg Ser Leu His Tyr
        370                 375                 380
Gln Phe Leu Ala Trp Tyr Met Tyr Ser Leu Pro Met Leu Leu Gln Leu
385                 390                 395                 400
Gly Gly Leu Pro Trp Tyr Ala Gln Thr Ala Leu Val Val Val His Glu
                405                 410                 415
Trp Cys Trp Asn Val Tyr Pro Ser Thr Ala Ala Ser Ser Leu Gly Leu
                420                 425                 430
Val Ala Val Leu Ala Thr Val Val Leu Ser Gln Leu Arg Cys Gly Phe
                435                 440                 445
Gly Lys Pro Lys Gln Glu
    450

<210> SEQ ID NO 15
<211> LENGTH: 432
<212> TYPE: PRT
<213> ORGANISM: Homo sapiens

<400> SEQUENCE: 15

Met Ala Ala Gly Leu Arg Lys Arg Gly Arg Ser Gly Ser Ala Ala Gln
1               5                   10                  15
Ala Glu Gly Leu Cys Lys Gln Trp Glu Arg Arg Leu Leu Leu Arg Glu
            20                  25                  30
Pro Arg Tyr Thr Leu Leu Val Ala Ala Cys Leu Cys Leu Ala Glu Val
        35                  40                  45
Gly Ile Thr Phe Trp Val Ile His Arg Val Ala Tyr Thr Glu Ile Asp
    50                  55                  60
Trp Lys Ala Tyr Met Ala Glu Val Glu Gly Val Ile Asn Gly Thr Tyr
65                  70                  75                  80
Asp Tyr Thr Gln Leu Gln Gly Asp Thr Gly Pro Leu Val Tyr Pro Ala
                85                  90                  95
Gly Phe Val Tyr Ile Phe Met Gly Leu Tyr Tyr Ala Thr Ser Arg Gly
            100                 105                 110
Thr Asp Ile Arg Met Ala Gln Asn Ile Phe Ala Val Leu Tyr Leu Ala
        115                 120                 125
Thr Leu Leu Leu Val Phe Leu Ile Tyr His Gln Thr Cys Lys Val Pro
    130                 135                 140
Pro Phe Val Phe Phe Met Cys Cys Ala Ser Tyr Arg Val His Ser
145                 150                 155                 160
Ile Phe Val Leu Arg Leu Phe Asn Asp Pro Val Ala Met Val Leu Leu
                165                 170                 175
Phe Leu Ser Ile Asn Leu Leu Leu Ala Gln Arg Trp Gly Trp Gly Cys
```

```
              180                 185                 190
Cys Phe Phe Ser Leu Ala Val Ser Val Lys Met Asn Val Leu Leu Phe
            195                 200                 205

Ala Pro Gly Leu Leu Phe Leu Leu Thr Gln Phe Gly Phe Arg Gly
        210                 215                 220

Ala Leu Pro Lys Leu Gly Ile Cys Ala Gly Leu Gln Val Val Leu Gly
225                 230                 235                 240

Leu Pro Phe Leu Leu Glu Asn Pro Ser Gly Tyr Leu Ser Arg Ser Phe
            245                 250                 255

Asp Leu Gly Arg Gln Phe Leu Phe His Trp Thr Val Asn Trp Arg Phe
        260                 265                 270

Leu Pro Glu Ala Leu Phe Leu His Arg Ala Phe His Leu Ala Leu Leu
        275                 280                 285

Thr Ala His Leu Thr Leu Leu Leu Phe Ala Leu Cys Arg Trp His
        290                 295                 300

Arg Thr Gly Glu Ser Ile Leu Ser Leu Leu Arg Asp Pro Ser Lys Arg
305                 310                 315                 320

Lys Val Pro Pro Gln Pro Leu Thr Pro Asn Gln Ile Val Ser Thr Leu
                325                 330                 335

Phe Thr Ser Asn Phe Ile Gly Ile Cys Phe Ser Arg Ser Leu His Tyr
            340                 345                 350

Gln Phe Tyr Val Trp Tyr Phe His Thr Leu Pro Tyr Leu Trp Ala
        355                 360                 365

Met Pro Ala Arg Trp Leu Thr His Leu Leu Arg Leu Leu Val Leu Gly
    370                 375                 380

Leu Ile Glu Leu Ser Trp Asn Thr Tyr Pro Ser Thr Ser Cys Ser Ser
385                 390                 395                 400

Ala Ala Leu His Ile Cys His Ala Val Ile Leu Leu Gln Leu Trp Leu
                405                 410                 415

Gly Pro Gln Pro Phe Pro Lys Ser Thr Gln His Ser Lys Lys Ala His
            420                 425                 430

<210> SEQ ID NO 16
<211> LENGTH: 464
<212> TYPE: PRT
<213> ORGANISM: Pichia pastoris

<400> SEQUENCE: 16

Met Pro Pro Ile Glu Pro Ala Glu Arg Pro Lys Leu Thr Leu Lys Asn
  1               5                  10                  15

Val Ile Gly Asp Leu Val Ala Leu Ile Gln Asn Val Leu Phe Asn Pro
             20                  25                  30

Asp Phe Ser Val Phe Val Ala Pro Leu Leu Trp Leu Ala Asp Ser Ile
         35                  40                  45

Val Ile Lys Val Ile Gly Thr Val Ser Tyr Thr Asp Ile Asp Phe
     50                  55                  60

Ser Ser Tyr Met Gln Gln Ile Phe Lys Ile Arg Gln Gly Glu Leu Asp
 65                  70                  75                  80

Tyr Ser Asn Ile Phe Gly Asp Thr Gly Pro Leu Val Tyr Pro Ala Gly
                 85                  90                  95

His Val His Ala Tyr Ser Val Leu Ser Trp Tyr Ser Asp Gly Gly Glu
            100                 105                 110

Asp Val Ser Phe Val Gln Gln Ala Phe Gly Trp Leu Tyr Leu Gly Cys
        115                 120                 125

Leu Leu Leu Ser Ile Ser Ser Tyr Phe Phe Ser Gly Leu Gly Lys Ile
```

```
                130             135             140
Pro Pro Val Tyr Phe Val Leu Leu Val Ala Ser Lys Arg Leu His Ser
145                 150                 155                 160

Ile Phe Val Leu Arg Leu Phe Asn Asp Cys Leu Thr Thr Phe Leu Met
                165                 170                 175

Leu Ala Thr Ile Ile Ile Leu Gln Gln Ala Ser Ser Trp Arg Lys Asp
                180                 185                 190

Gly Thr Thr Ile Pro Leu Ser Val Pro Asp Ala Ala Asp Thr Tyr Ser
                195                 200                 205

Leu Ala Ile Ser Val Lys Met Asn Ala Leu Leu Tyr Leu Pro Ala Phe
210                 215                 220

Leu Leu Leu Ile Tyr Leu Ile Cys Asp Glu Asn Leu Ile Lys Ala Leu
225                 230                 235                 240

Ala Pro Val Leu Val Leu Ile Leu Val Gln Val Gly Val Gly Tyr Ser
                245                 250                 255

Phe Ile Leu Pro Leu His Tyr Asp Asp Gln Ala Asn Glu Ile Arg Ser
                260                 265                 270

Ala Tyr Phe Arg Gln Ala Phe Asp Phe Ser Arg Gln Phe Leu Tyr Lys
                275                 280                 285

Trp Thr Val Asn Trp Arg Phe Leu Ser Gln Glu Thr Phe Asn Asn Val
290                 295                 300

His Phe His Gln Leu Leu Phe Ala Leu His Ile Ile Thr Leu Val Leu
305                 310                 315                 320

Phe Ile Leu Lys Phe Leu Ser Pro Lys Asn Ile Gly Lys Pro Leu Gly
                325                 330                 335

Arg Phe Val Leu Asp Ile Phe Lys Phe Trp Lys Pro Thr Leu Ser Pro
                340                 345                 350

Thr Asn Ile Ile Asn Asp Pro Glu Arg Ser Pro Asp Phe Val Tyr Thr
                355                 360                 365

Val Asn Ala Thr Thr Asn Leu Ile Gly Val Leu Phe Ala Arg Ser Leu
370                 375                 380

His Tyr Gln Phe Leu Ser Trp Tyr Ala Phe Ser Leu Pro Tyr Leu Leu
385                 390                 395                 400

Tyr Lys Ala Arg Leu Asn Phe Ile Ala Ser Ile Val Tyr Ala Ala
                405                 410                 415

His Glu Tyr Cys Trp Leu Val Phe Pro Ala Thr Glu Gln Ser Ser Ala
                420                 425                 430

Leu Leu Val Ser Ile Leu Leu Leu Ile Leu Ile Phe Thr Asn
                435                 440                 445

Glu Gln Leu Phe Pro Ser Gln Ser Val Pro Ala Glu Lys Lys Asn Thr
450                 455                 460

<210> SEQ ID NO 17
<211> LENGTH: 458
<212> TYPE: PRT
<213> ORGANISM: Saccharomyces cerevisiae

<400> SEQUENCE: 17

Met Glu Gly Glu Gln Ser Pro Gln Gly Glu Lys Ser Leu Gln Arg Lys
1               5                   10                  15

Gln Phe Val Arg Pro Pro Leu Asp Leu Trp Gln Asp Leu Lys Asp Gly
                20                  25                  30

Val Arg Tyr Val Ile Phe Asp Cys Arg Ala Asn Leu Ile Val Met Pro
                35                  40                  45

Leu Leu Ile Leu Phe Glu Ser Met Leu Cys Lys Ile Ile Ile Lys Lys
```

-continued

```
            50                  55                  60
Val Ala Tyr Thr Glu Ile Asp Tyr Lys Ala Tyr Met Glu Gln Ile Glu
 65                  70                  75                  80

Met Ile Gln Leu Asp Gly Met Leu Asp Tyr Ser Gln Val Ser Gly Gly
                 85                  90                  95

Thr Gly Pro Leu Val Tyr Pro Ala Gly His Val Leu Ile Tyr Lys Met
            100                 105                 110

Met Tyr Trp Leu Thr Glu Gly Met Asp His Val Glu Arg Gly Gln Val
            115                 120                 125

Phe Phe Arg Tyr Leu Tyr Leu Leu Thr Leu Ala Leu Gln Met Ala Cys
            130                 135                 140

Tyr Tyr Leu Leu His Leu Pro Pro Trp Cys Val Val Leu Ala Cys Leu
145                 150                 155                 160

Ser Lys Arg Leu His Ser Ile Tyr Val Leu Arg Leu Phe Asn Asp Cys
                165                 170                 175

Phe Thr Thr Leu Phe Met Val Val Thr Val Leu Gly Ala Ile Val Ala
            180                 185                 190

Ser Arg Cys His Gln Arg Pro Lys Leu Lys Lys Ser Leu Ala Leu Val
            195                 200                 205

Ile Ser Ala Thr Tyr Ser Met Ala Val Ser Ile Lys Met Asn Ala Leu
210                 215                 220

Leu Tyr Phe Pro Ala Met Met Ile Ser Leu Phe Ile Leu Asn Asp Ala
225                 230                 235                 240

Asn Val Ile Leu Thr Leu Leu Asp Leu Val Ala Met Ile Ala Trp Gln
            245                 250                 255

Val Ala Val Ala Val Pro Phe Leu Arg Ser Phe Pro Gln Gln Tyr Leu
            260                 265                 270

His Cys Ala Phe Asn Phe Gly Arg Lys Phe Met Tyr Gln Trp Ser Ile
            275                 280                 285

Asn Trp Gln Met Met Asp Glu Glu Ala Phe Asn Asp Lys Arg Phe His
            290                 295                 300

Leu Ala Leu Leu Ile Ser His Leu Ile Ala Leu Thr Thr Leu Phe Val
305                 310                 315                 320

Thr Arg Tyr Pro Arg Ile Leu Pro Asp Leu Trp Ser Ser Leu Cys His
            325                 330                 335

Pro Leu Arg Lys Asn Ala Val Leu Asn Ala Asn Pro Lys Thr Ile
            340                 345                 350

Arg Phe Val Leu Ile Ala Ser Asn Phe Ile Gly Val Leu Phe Ser Arg
            355                 360                 365

Ser Leu His Tyr Gln Phe Leu Ser Trp Tyr His Trp Thr Leu Pro Ile
            370                 375                 380

Leu Ile Phe Trp Ser Gly Met Pro Phe Phe Val Gly Pro Ile Trp Tyr
385                 390                 395                 400

Val Leu His Glu Trp Cys Trp Asn Ser Tyr Pro Pro Asn Ser Gln Ala
            405                 410                 415

Ser Thr Leu Leu Leu Ala Leu Asn Thr Val Leu Leu Leu Leu Ala
            420                 425                 430

Leu Thr Gln Leu Ser Gly Ser Val Ala Leu Ala Lys Ser His Leu Arg
            435                 440                 445

Thr Thr Ser Ser Met Glu Lys Lys Leu Asn
            450                 455
```